(12) United States Patent
Upton et al.

(10) Patent No.: US 11,450,000 B2
(45) Date of Patent: Sep. 20, 2022

(54) IMAGE ANALYSIS FOR SCORING MOTION OF A HEART WALL

(71) Applicant: OXFORD UNIVERSITY INNOVATION LIMITED, Oxford (GB)

(72) Inventors: Ross Upton, Oxford (GB); Paul Leeson, Oxford (GB); Edmund Wilkes, Oxford (GB); Deborah Markham, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 68 days.

(21) Appl. No.: 16/772,550

(22) PCT Filed: Dec. 12, 2018

(86) PCT No.: PCT/EP2018/084640
§ 371 (c)(1),
(2) Date: Jun. 12, 2020

(87) PCT Pub. No.: WO2019/115650
PCT Pub. Date: Jun. 20, 2019

(65) Prior Publication Data
US 2020/0388037 A1    Dec. 10, 2020

(30) Foreign Application Priority Data
Dec. 13, 2017    (GB) .................................. 1720789

(51) Int. Cl.
*G06T 7/00* (2017.01)
*G06T 7/62* (2017.01)
(Continued)

(52) U.S. Cl.
CPC .......... *G06T 7/0016* (2013.01); *A61B 8/0883* (2013.01); *A61B 8/5223* (2013.01);
(Continued)

(58) Field of Classification Search
CPC .......... A61B 8/0883; A61B 8/14; A61B 8/463; A61B 8/5223; A61B 8/543;
(Continued)

(56) References Cited

U.S. PATENT DOCUMENTS

| 5,776,063 A | 7/1998 | Dittrich et al. |
| 6,674,879 B1 | 1/2004 | Weisman et al. |

(Continued)

FOREIGN PATENT DOCUMENTS

| EP | 1522875 A1 | 4/2005 |
| JP | 2005-237555 A | 9/2005 |

(Continued)

OTHER PUBLICATIONS

"Patents Act 1977: Intention to Grant under Section 18(4)", GB Application No. GB1720789.5, dated Mar. 24, 2021, 2 pp.
(Continued)

*Primary Examiner* — Manuchehr Rahmjoo
(74) *Attorney, Agent, or Firm* — Myers Bigel, P.A.

(57) ABSTRACT

The present disclosure relates to a system (100) for scoring motion of a heart wall (214, 218). The system (100) includes an imaging system (102) operable to acquire a first image (230) of the heart wall (214, 218) at a first time and a second image (240) of the heart wall (214, 218) at a second time. A processor (108) is provided to identify a first set of contour data in the first image (230); and a second set of contour data in the second image (240). The processor (108) defines at least one element (Ei) representing a cardiac cyclic change in a section of the heart wall (214, 218) in dependence on the first and second sets of contour data. Each element (Ei) is
(Continued)

analysed to generate at least one metric which is compared with a reference data model to score the motion of the corresponding section of the heart wall (214, 218). The disclosure also relates to a method of scoring motion of a heart wall (214, 218); and a non-transitory computer-readable medium.

20 Claims, 14 Drawing Sheets

(51) Int. Cl.
    *G06T 7/13*         (2017.01)
    *G06T 7/246*       (2017.01)
    *G16H 50/50*       (2018.01)
    *G16H 50/30*       (2018.01)
    *G16H 50/70*       (2018.01)
    *G16H 30/40*       (2018.01)
    *A61B 8/08*         (2006.01)
    *G16H 70/60*       (2018.01)
    *G16H 50/20*       (2018.01)
    *A61B 8/14*         (2006.01)
    *A61B 8/00*         (2006.01)

(52) U.S. Cl.
    CPC ............... *G06T 7/13* (2017.01); *G06T 7/248* (2017.01); *G06T 7/62* (2017.01); *G16H 30/40* (2018.01); *G16H 50/30* (2018.01); *G16H 50/50* (2018.01); *G16H 50/70* (2018.01); *A61B 8/14* (2013.01); *A61B 8/543* (2013.01); *G06T 2207/30048* (2013.01); *G06T 2207/30241* (2013.01); *G16H 50/20* (2018.01); *G16H 70/60* (2018.01)

(58) Field of Classification Search
    CPC . G06T 2207/10132; G06T 2207/30048; G06T 2207/30241; G06T 7/0016; G06T 7/13; G06T 7/248; G06T 7/62; G16H 30/40; G16H 50/20; G16H 50/30; G16H 50/50; G16H 50/70; G16H 70/60
    See application file for complete search history.

(56) References Cited

U.S. PATENT DOCUMENTS

| | | | |
|---|---|---|---|
| 8,077,944 | B2 | 12/2011 | Schummers |
| 2004/0153128 | A1 | 8/2004 | Suresh et al. |
| 2005/0020903 | A1 | 1/2005 | Krishnan et al. |
| 2005/0059876 | A1 | 3/2005 | Krishnan et al. |
| 2006/0074315 | A1 | 4/2006 | Liang et al. |
| 2007/0299479 | A1 | 12/2007 | Saksena |
| 2009/0308745 | A1 | 12/2009 | McLeod |
| 2010/0198072 | A1 | 8/2010 | Abe et al. |
| 2011/0035195 | A1 | 2/2011 | Subbiah et al. |
| 2011/0056876 | A1 | 3/2011 | Ide et al. |
| 2011/0243401 | A1 | 10/2011 | Zabair et al. |
| 2016/0004933 | A1 | 1/2016 | Hu et al. |
| 2019/0247016 | A1 | 8/2019 | Upton et al. |

FOREIGN PATENT DOCUMENTS

| | | |
|---|---|---|
| WO | 2007/054861 A2 | 5/2007 |
| WO | 2015/168792 A1 | 11/2015 |
| WO | 2017/216545 A1 | 12/2017 |
| WO | 2019/115652 A1 | 6/2019 |

OTHER PUBLICATIONS

"Communication under Rule 71(3) EPC, including text intended for grant", EP Application No. 18819098.7, dated Feb. 22, 2021, 112 pp.

"Communication under Rule 71(3) EPC, including text intended for grant", EP Application No. 18819098.7, dated Aug. 5, 2021, 112 pp.

"Patents Act 1977: Patents Rules 2007 / Notification of Grant: Patent Serial No. GB2569332", GB Application No. GB1720789.5, dated May 11, 2021, 2 pp.

Patents Act 1977: Combined Search and Examination Report under Sections 17 and 18(3), UKIPO Application No. GB1720789.5, dated Jun. 13, 2018, 6 pp.

International Search Report and Written Opinion of the International Searching Authority, International Application No. PCT/EP2018/084640, dated Feb. 14, 2019, 10 pp.

International Preliminary Report on Patentability, International Application No. PCT/EP2018/084640, dated Apr. 6, 2020, 13 pp.

Patents Act 1977: Combined Search and Examination Report under Sections 17 and 18(3), UKIPO Application No. GB1720791.1, dated Jun. 13, 2018, 9 pp.

International Search Report and Written Opinion of the International Searching Authority, International Application No. PCT/EP2018/084642, dated Apr. 3, 2019.

International Preliminary Report on Patentability, International Application No. PCT/EP2018/084642, dated Apr. 24, 2020, 15 pp.

International Search Report and Written Opinion of the International Searching Authority, International Application No. PCT/GB2017/051720, dated Aug. 14, 2017, 11 pp.

International Preliminary Report on Patentability, International Application No. PCT/GB2017/051720, dated Dec. 27, 2018, 20 pp.

Assmann et al., "Comparison of Models for Quantitative Left Ventricular Wall Motion Analysis from Two-Dimensional Echocardiograms During Acute Myocardial Infarction", The American Journal of Cardiology, vol. 71, Jan. 1, 1993, pp. 1262-1269.

Elalfi et al., "Artificial Neural Networks in Medical Images for Diagnosis Heart Valve Diseases", IJCSI International Journal of Computer Science Issues, vol. 10, Issue 5, No. 1, Sep. 2013, pp. 83-90.

El-Kader et al., "Echocardiography heart diagnosis using Artificial Neural Networks", IJCSNS International Journal of Computer Science and Network Security, vol. 12, No. 12, Dec. 2012, pp. 141-148.

Mansor et al., "Wall Motion Classification of Stress Echocardiography Based on Combined Rest-and-Stress Data", Medical Image Computing and Computer-Assisted Intervention—MICCAI 2008, Springer, Berlin, Heidelberg, vol. 5242, Jan. 1, 2008, pp. 139-146.

Narula et al., "Machine-Learning Algorithms to Automate Morphological and Functional Assessment in 2D Echocardiography", Journal of the American College of Cardiology, vol. 68, No. 21, Nov. 29, 2016, pp. 2287-2295.

Ortiz et al., "One-Year Mortality Prognosis in Heart Failure: A Neural Network Approach Based on Echocardiographic Data", Journal of the American College of Cardiology, vol. 26, No. 7, Dec. 1995, pp. 1586-1593.

Slomka et al., "Cardiac imaging: working towards fully-automated machine analysis & interpretation", Expert Review of Medical Devices, vol. 14, No. 3, Mar. 2017, pp. 197-212.

Steinhard et al., "OP18.11: Quantification of regional atrial contraction in the fetal heart using the parameters strain and velocity—a tissue Doppler imaging (TDI) study", Ultrasound in Obstetrics & Gynecology, vol. 30, Issue 4, Oct. 2007, p. 519.

Sudarshan et al., "Automated Identification of Infarcted Myocardium Tissue Characterization using Ultrasound Images: A Review", IEEE Reviews In Biomedical Engineering, vol. 8, Apr. 24, 2014, pp. 86-97.

"Examination report under sections 12 & 13 of the Patents Act, 1970 and the Patents Rules, 2003", IN Application No. 202017024913, dated Apr. 1, 2022, 6 pp.

"Examination report under sections 12 & 13 of the Patents Act, 1970 and the Patents Rules, 2003", IN Application No. 202017028646, dated Apr. 19, 2022, 7 pp.

"Notification of Reason for Refusal and English language translation", JP Application No. 2020-552120, dated Mar. 8, 2022, 6 pp.

"Invitation to Respond to Written Opinion and Written Opinion" SG Application No. 11202005348R, dated Apr. 7, 2022, 7 pp.

(56) References Cited

OTHER PUBLICATIONS

"Notification of Reason for Refusal and English language translation", KR Application No. 10-2020-7020232, dated Apr. 19, 2022, 7 pp.

Wall motion score

Wall motion score

IMAGE ANALYSIS FOR SCORING MOTION OF A HEART WALL

RELATED APPLICATIONS

This application is a 35 U.S.C. § 371 national stage application of PCT Application No. PCT/EP2018/084640, filed on Dec. 12, 2018, which claims priority from Great Britain Patent Application No. 1720789.5 filed on Dec. 13, 2017, the contents of which are incorporated herein by reference in their entireties. The above-referenced PCT International Application was published in the English language as International Publication No. WO 2019/115650 A1 on Jun. 20, 2019.

TECHNICAL FIELD

The present disclosure relates to a method and apparatus for analysing images. More particularly, but not exclusively, the present disclosure relates to a system and method for scoring motion of a heart wall.

BACKGROUND

Two-dimensional (2D) echocardiography is an imaging technique through which the motion of the heart can be assessed under different conditions, for example resting or stress conditions. The analysis may be performed under other conditions including, for example, an intermediate stress stage and/or a recovery stage. This can highlight areas of the heart that are hypo- or dysfunctional, and can thus identify patients in which medical intervention may be necessary. A typical model of the left ventricle comprises sixteen (16) segments which are visible using different 2D images of the heart. Other models of the left ventricle may, for example, comprise seventeen (17) segments. The apical inferior segment, mid inferior segment, basal inferior segment, apical anterior segment, mid anterior segment and basal anterior segment are visible in an apical two chamber image. The apical septum segment, mid septum segment, basal septum segment, apical lateral segment, mid lateral segment and basal lateral segment are visible in an apical four chamber image. The anteroseptum segment, inferoseptum segment, mid inferior segment, mid anterior segment, anterolateral segment and inferolateral segment are visible in a parasternal short axis image. The apical lateral segment, the mid inferolateral segment, basal inferolateral segment, the apical septum segment, the mid septum segment, and the basal septum segment are visible in an apical three chamber image (or parasternal long axis image). The behaviour of each segment can be viewed in different sections of the left ventricle. The motion of each segment of the myocardium under different conditions (such as resting and stress conditions) is currently determined by interpretation of the 2D echocardiography data by an expert cardiologist. This is performed in a categorical manner. For example, each section of the myocardial wall may be classified as having one of the following reference wall motion scores: normal ("1"), hypokinetic ("2"), akinetic ("3"), dyskinetic ("4"), and unable to score ("X"). Other classifications may be used, for example defining five (5) or seven (7) discrete scores for each segment. The known techniques rely on subjective classification and may prove a time consuming exercise.

It has been recognised that image quantification tools need to allow for the following: (i) changing underlying disease pathophysiology over time; (ii) disease pathology variations with geographical location and changing nature of the patient population being referred for the test; and (iii) the changing understanding of what is defined as disease or what is disease causing.

At least in certain embodiments, the present invention seeks to provide an improved method and apparatus for analysing images.

SUMMARY OF THE INVENTION

Aspects of the present invention relate to a system for scoring motion of a heart wall, a method of scoring motion of a heart wall, and a non-transitory computer-readable medium as claimed in the appended claims.

According to an aspect of the present invention there is provided a system for scoring motion of a heart wall, the system comprising:
  an imaging system operable to acquire a first image of the heart wall at a first time and a second image of the heart wall at a second time;
  a processor configured to:
    identify a first set of contour data in the first image;
    identify a second set of contour data in the second image;
    in dependence on the first and second sets of contour data, define at least one element representing a cardiac cyclic change in a section of the heart wall;
    analyse each element to generate at least one metric; and
    compare the at least one metric with a reference data model to score the motion of the corresponding section of the heart wall.

At least in certain embodiments, the system described herein may partially or completely automate scoring of the wall motion in dependence on the first and second images. Furthermore, the system described herein may implement a scoring system which is continuous, rather than a categorical model. At least in certain embodiments, the motion of the heart wall may be scored on a substantially continuous scale. The scoring may be performed in dependence on one metric or in dependence on a plurality of metrics.

Each element represents a change in a cardiac cyclic parameter of a section of the heart wall. The elements are each defined in at least two dimensions. In a variant, the elements could each be defined in three dimensions.

The at least one element represents a cardiac cyclic change of a section of the heart wall. The heart wall may be modelled by a plurality of segments. Each element may represent the cardiac cyclic change in one of said segments. Alternatively, each element may represent the cardiac cyclic change in a portion of one of said segments (i.e. in a subsegment). It will be understood that the elements may be unrelated to the segments of a conventional model. For example, the elements may subdivide the heart wall into eight (8) regions.

The system may score motion of a ventricle of the heart. For example, the system may score motion of a left ventricle of the heart. As described herein, the left ventricle of the heart may be modelled by sixteen (16) segments. Each element may represent the cardiac cyclic change in one of the segments of an internal wall of the left ventricle. Alternatively, each element may represent the cardiac cyclic change in a portion of one of said segments (i.e. in a subsegment) of an internal wall of the left ventricle.

The reference data model may be predefined. The reference data model may be generated in dependence on analysis of historic data, for example derived from analysis of a plurality of images acquired for multiple individuals. The at least one metric generated for each element may be compared with the reference data model for a corresponding section of the heart wall. The reference data model may be generated for each segment of a model of the heart wall. The at least one metric may be compared with the reference data model for a corresponding segment of the heart wall.

The first set of contour data may comprise a plurality of first contour points. The first contour points may be connected to each other to form a first contour. The first contour points may be connected to each other by a straight line and/or a curved line. The first contour may comprise a first continuous curve.

The second set of contour data may comprise a plurality of second contour points. The second contour points may be connected to each other to form a second contour. The second contour points may be connected to each other by a straight line and/or a curved line. The second contour may comprise a second continuous curve.

The first set of contour data may be identified in dependence on user inputs, for example user inputs to specify contour points in the first and second images. Alternatively, the processor may be configured to analyse the first and second images to identify the first and second sets of contour data. The processor may, for example, utilise image processing techniques to identify the first and second sets of contour data. The image processing techniques may, for example, comprise motion segmentation to identify the first and second contour points; and/or boundary detection techniques to identify the first and second contour points and/or the first and second contours.

The processor may be configured to identify a plurality of pairs of contour points. Each pair of contour points may relate to a corresponding feature in the first and second sets of contour data. Each pair may consist of corresponding first and second contour points. The first and second contour points may relate to a single feature present in the first and second sets of contour data.

Each element may comprise at least first and second pairs of contour points. The contour points making up each pair may define vertices of the element.

The analysis of each element comprises determining a distance between the contour points in each pair and calculating a mean distance between the contour points for each element. The mean distance of each element may be normalised to a total perimeter of the first or second sets of contour data.

Each element may comprise opposing first and second sides corresponding to motion trajectories of the contour points.

The analysis of each element may comprise determining an area of the element. The area may correspond to an area enclosed by the first and second sets of contour data. The area may, for example, correspond to an area between end-diastolic and end-systolic contours. The determined area may be normalised. For example, the area of each element may be normalised to the total area of the end-diastolic data points.

The analysis of each element may comprise determining a rectangularity of each element. The rectangularity of each element may be calculated as the ratio between the area of each element and the area of its minimum bounding rectangle.

The analysis of each element may comprise determining a solidity of each element. A solidity of each element may be calculated as the ratio between the element's area and the area of its convex hull.

The processor may be configured to perform scoring on a continuous scale. The processor may be configured to output a score to classify or grade the heart wall motion. Alternatively, or in addition, the processor may be configured to output an RGB value to represent the scoring as a colour.

The imaging system may be configured to generate three-dimensional images. The first and second images may be three-dimensional images. The at least one element may be defined in three dimensions. The imaging system may be configured to generate two-dimensional images. The first and second images may comprise two-dimensional images of the heart wall. The at least one element may be defined in two dimensions.

Each element may comprise an irregular shape, for example comprising one or more curved sides. Alternatively, each element may comprise a polygon.

The processor may be configured to score the motion of the heart wall during at least one condition. The processor may be configured to score the motion of the heart wall during a plurality of conditions. The scoring may be performed during one or more of the following set: a rest condition, a stress condition, an intermediate stress condition, a recovery condition and so on. The imaging system may be operable to acquire first and second images of the heart wall under stress conditions. The imaging system may be operable to acquire first and second images of the heart wall under rest conditions. The scoring may be performed in respect of the images acquired under different conditions, for example under stress and rest conditions.

The first image may comprise an end systole image and the second image may comprise an end diastole image. The first set of contour data may comprise end systole contour data and the second set of contour data may comprise end diastole data.

According to a further aspect of the present invention there is provided a method of scoring motion of a heart wall, the method comprising:
  acquiring a first image of the heart wall at a first time and a second image of the heart wall at a second time;
  identifying a first set of contour data in the first image;
  identifying a second set of contour data in the second image;
  in dependence on the first and second sets of contour data, defining at least one element representing a cardiac cyclic change in a section of the heart wall;
  analysing each element to generate at least one metric; and
  comparing the at least one metric with a reference data model to score the motion of the corresponding section of the heart wall.

The method may comprise identifying a plurality of pairs of contour points. Each pair of contour points may relate to corresponding features in the first and second sets of contour data.

Each element may comprise at least first and second pairs of contour points. The contour points in each pair may define vertices of the element.

The analysis of each element may comprise determining a distance between the contour points in each pair and calculating a mean distance between the contour points for each element.

The method may comprise determining motion trajectories of each contour point. The motion trajectories may be determined with reference to the first and second images, for example by comparing the position of the contour points in each pair. Alternatively, or in addition, the motion trajectories may be generated in dependence on one or more interim images acquired between said first and second times. Each element may comprise opposing first and second sides corresponding to motion trajectories of the image elements.

The analysis of each element may comprise determining an area of the element. The area may correspond to an area enclosed by the first and second sets of contour data. The area may, for example, correspond to an area between end-diastolic and end-systolic contours. The determined area may be normalised. For example, the area of each element may be normalised to the total area of the end-diastolic data points.

The analysis of each element may comprise determining a rectangularity of each element. The rectangularity of each element may be calculated as the ratio between the area of each element and the area of its minimum bounding rectangle.

The analysis of each element may comprise determining a solidity of each element. A solidity of each element may be calculated as the ratio between the element's area and the area of its convex hull.

The scoring may be performed on a continuous scale.

The first and second images may comprise three-dimensional images of the heart wall. The first and second images may comprise two-dimensional images of the heart wall.

Each element may comprise a polygon. The polygon may be defined in two dimensions or three dimensions.

The method may comprise scoring the motion of the heart wall during a rest condition and during a stress condition.

The first image may comprise an end systole image and the second image may comprise an end diastole image. The first set of contour data may comprise end systole contour data and the second set of contour data may comprise end diastole data.

According to a further aspect of the present invention there is provided a system for generating a reference data model, the system comprising a processor configured to:
  analyse a plurality of sets of echocardiograph images, each set comprising at least first and second echocardiograph images, the analysis comprising identifying an end systolic image and an end diastolic image within each set;
  compare the end systolic image and the end diastolic image in each set to identify a cardiac cyclic change;
  calculate at least one metric in dependence on the identified cardiac cyclic change in respect of each set;
  acquire outcome data associated with at least some of the sets of echocardiograph images; and
  compile the reference data model in dependence on the calculated metrics and the associated outcome data.

According to a further aspect of the present invention there is provided a method of generating a reference data model, the method comprising:
  analysing a plurality of sets of echocardiograph images, each set comprising at least first and second echocardiograph images, the analysis comprising identifying an end systolic image and an end diastolic image within each set;
  comparing the end systolic image and the end diastolic image in each set to identify a cardiac cyclic change;
  in respect of each set, calculate at least one metric in dependence on the identified cardiac cyclic change;
  acquiring outcome data associated with at least some of the sets of echocardiograph images; and
  compiling the reference data model in dependence on the calculated metrics and the associated outcome data.

According to a further aspect of the present invention there is provided a non-transitory computer-readable medium having a set of instructions stored therein which, when executed, cause a processor to perform the method described herein.

Any control unit or controller described herein may suitably comprise a computational device having one or more electronic processors. The system may comprise a single control unit or electronic controller or alternatively different functions of the controller may be embodied in, or hosted in, different control units or controllers. As used herein the term "controller" or "control unit" will be understood to include both a single control unit or controller and a plurality of control units or controllers collectively operating to provide any stated control functionality. To configure a controller or control unit, a suitable set of instructions may be provided which, when executed, cause said control unit or computational device to implement the control techniques specified herein. The set of instructions may suitably be embedded in said one or more electronic processors. Alternatively, the set of instructions may be provided as software saved on one or more memory associated with said controller to be executed on said computational device. The control unit or controller may be implemented in software run on one or more processors. One or more other control unit or controller may be implemented in software run on one or more processors, optionally the same one or more processors as the first controller. Other suitable arrangements may also be used.

Within the scope of this application it is expressly intended that the various aspects, embodiments, examples and alternatives set out in the preceding paragraphs, in the claims and/or in the following description and drawings, and in particular the individual features thereof, may be taken independently or in any combination. That is, all embodiments and/or features of any embodiment can be combined in any way and/or combination, unless such features are incompatible. The applicant reserves the right to change any originally filed claim or file any new claim accordingly, including the right to amend any originally filed claim to depend from and/or incorporate any feature of any other claim although not originally claimed in that manner.

BRIEF DESCRIPTION OF THE DRAWINGS

One or more embodiments of the present invention will now be described, by way of example only, with reference to the accompanying figures, in which.

DETAILED DESCRIPTION

An echocardiography system 100 in accordance with an embodiment of the present invention will now be described with reference to the accompanying figures. The echocardiography system 100 is operable to analyse images of a heart 200 and to score the cardiac cyclic motion.

Figure 1:
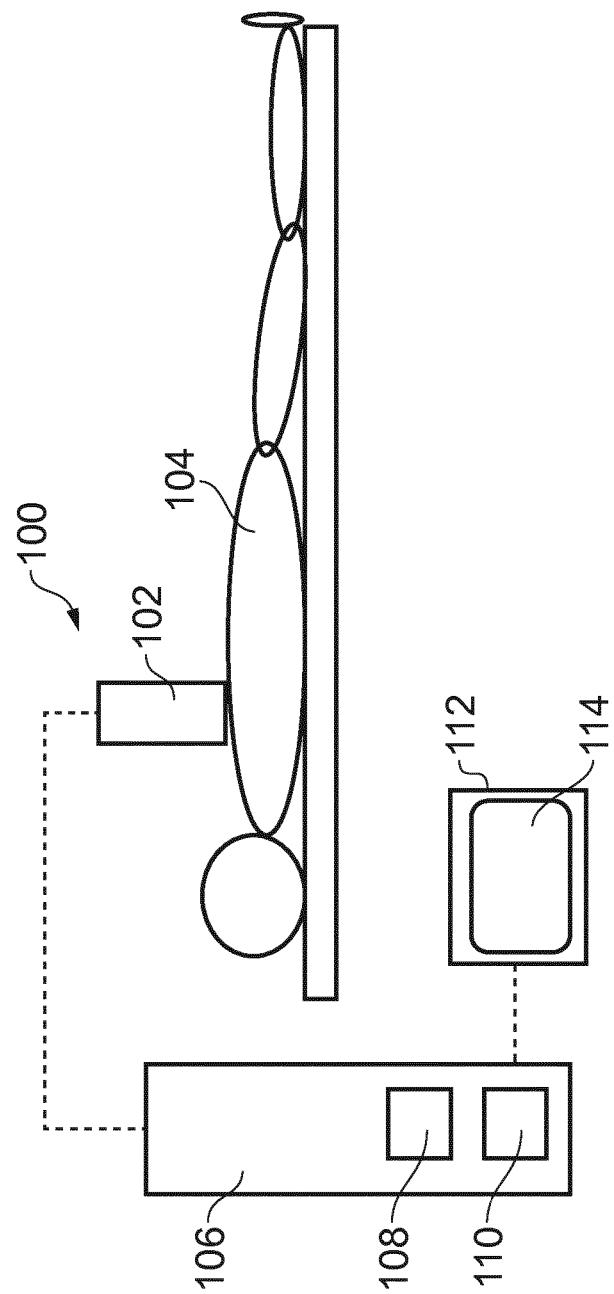
FIG. 1 is a schematic view of an echocardiography system according to an embodiment of the invention.

As shown in FIG. 1, the echocardiography system 100 comprises a transducer array 102 arranged to be located close to the body of a patient 104, typically as close to the heart as possible, a processing unit 106 which includes a processor 108 which may be a digital electronic processor, a memory 110 such as a hard disk, and a display 112, such as a flat screen monitor or LED display. The system may further include a user input device, for example a touch-screen 114 integrated into the display 112, which provides a user input allowing a user to provide inputs to the echocardiography system 100. Other user inputs such as a mouse, touchpad or keyboard may of course be used. The processing unit 106 is connected to the transducer array 102 and is arranged to control the transducer array as a phased array so as to emit an ultrasound beam which scans across the patient in a series of pulses, and detect reflected ultrasound from the heart from each pulse. One scan of the heart builds up a single image, and the scan is repeated at typically 25 to 50 images per second to build up a real time video image of the heart showing its movement during the cardiac cycle. Each image may be stored in the memory 110 as an image data set which may comprise, for example, intensity values for each of the pixels of which the image is made up. While the system is described herein in general terms, suitable echocardiography systems include, for example the Philips Epic iE33, GE vivid e9, or portable systems such as the Philips CX50, or hand-held systems.

The process of echocardiography is well known and is not described herein in detail. There are several different imaging methods, but the echocardiography system 100 in accordance with the present embodiment uses two-dimensional imaging. It is known to provide images on several different planes through the heart, which show different aspects of the four main chambers of the heart, the left ventricle (LV), right ventricle (RV), left atrium (LA) and right atrium (RA). Such views include, for example, an apical four chamber view, an apical two chamber view, an apical three chamber view and parasternal long and short axis views. In each case, while a single still image can be obtained, typically a series of views is acquired over the cycle of the heart so that its movement can be recorded and analysed. The echocardiography system 100 may utilise one or more of the aforementioned views to score the cardiac cyclic motion of the heart 200.

Figure 2:
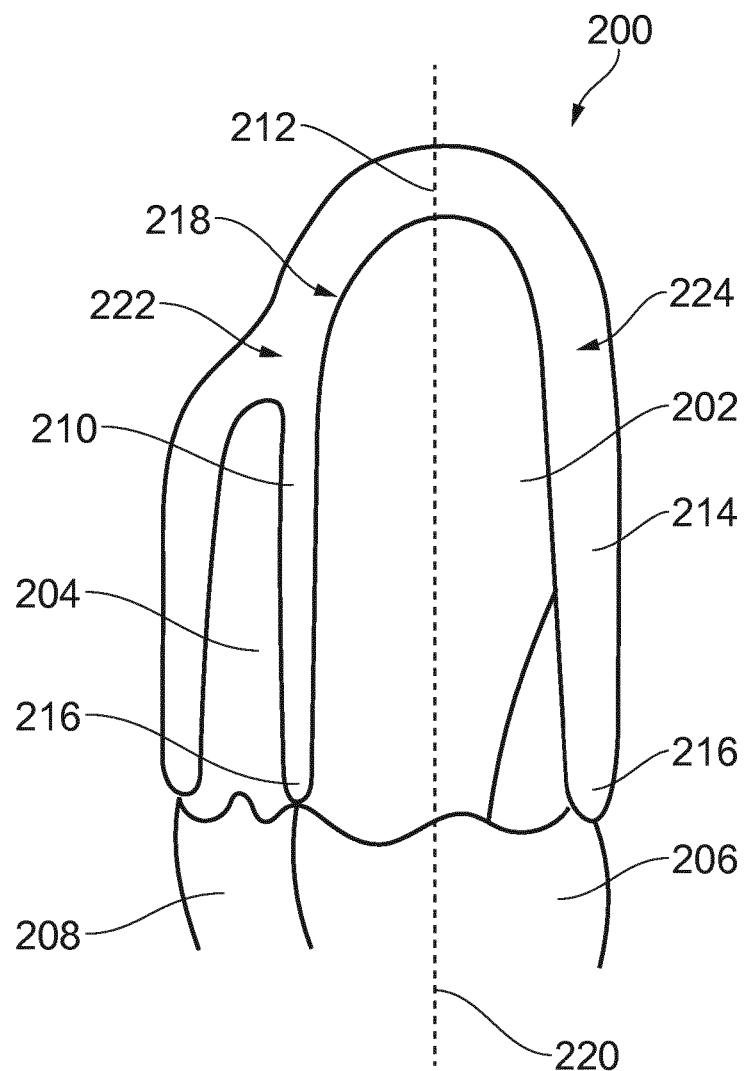
FIG. 2 shows schematically a four-chamber view of a heart.

A four-chamber apical image of a heart 200 is shown in FIG. 2 by way of example. The image comprises a 2D plane of the heart 200. The image shows a left ventricle (LV) 202, a right ventricle (RV) 204, a left atrium 206, a right atrium 208 and a septum 210. An apex 212, a lateral wall 214, a base 216 and an inner wall 218 of the left ventricle 202 are also visible in the four-chamber apical view. A longitudinal axis 220 of the left ventricle 202 extends through the apex 212. The left ventricle 202 has first and second sides 222, 224 disposed on opposing sides of the longitudinal axis 220.

The processing unit 106 analyses the four-chamber apical image to implement the scoring techniques described herein. Alternatively, or in addition, the processing unit 106 may utilise one or more of the following: a two-chamber apical image, a parasternal short axis image and a three-chamber apical view. Other echocardiograph images could be used by the processing unit 106 to implement the scoring techniques described herein. The processing unit 106 may use various combinations of the echocardiograph images provide scoring for the sixteen (16) segments of the left ventricle. The processing unit 106 may analyse a plurality of images and score the cardiac cyclic motion in dependence on the metrics for multiple images. The processing unit 106 may qualitatively assess the available images and prioritise an image determined as providing a clearer representation of the cardiac cyclic motion of a particular section of the heart wall. A Cartesian coordinate system is defined comprising a vertical axis (referred to as the y axis herein) extending through the apex 212 of the left ventricle 202 and extending along its longitudinal axis, and a horizontal axis (referred to as the x axis herein) through the mid-point of the left ventricle 202 half way between the apex 212 and the base 216.

Figure 3:
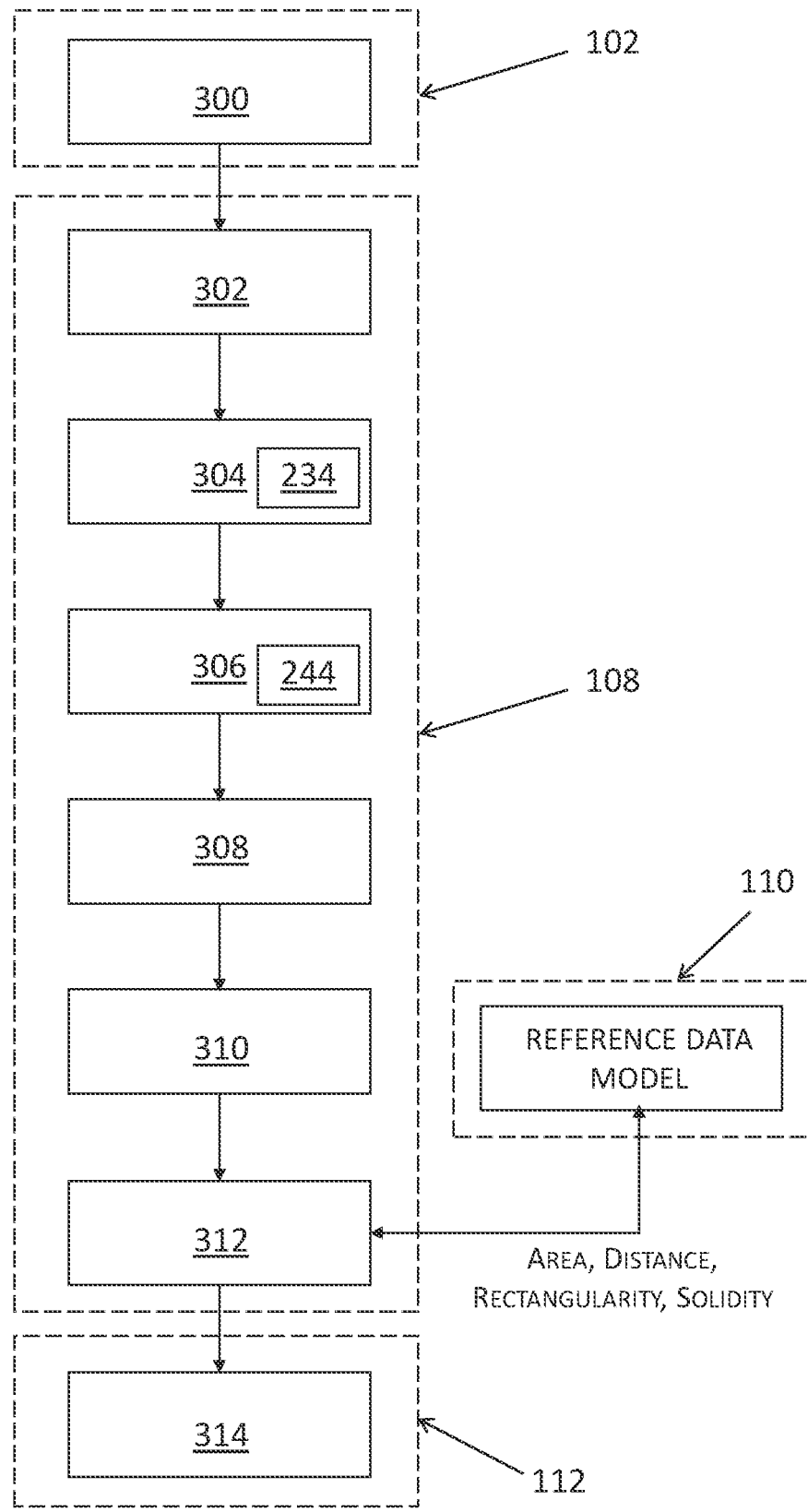
FIG. 3 is a flow diagram showing the main steps of a diagnostic method performed by the system of FIG. 1.

A block diagram representing operation of the echocardiography system 100 is shown in FIG. 3. The echocardiography system 100 is arranged to acquire a sequence of 2D images and store them in memory 110 (BLOCK 300). The images may be acquired over a single cardiac cycle, and may include for example between ten (10) and fifty (50) images covering one cycle. The echocardiography system 100 may perform a single scan or more than one scan. For example, the echocardiography system 100 may perform first and second scans. The first scan may be performed when the patient is under rest conditions and the second scan may be performed when the patient is under stress condition. The echocardiography system 100 may optionally perform one or more intermediate scan between the rest condition and the stress condition, for example during a recovery phase as heart rate returns to normal after being stressed. The acquisition of the images can be carried out on a conventional echocardiography system. The subsequent analysis of the images can be carried out using the same processing unit 106 that forms part of the echocardiography system as shown in FIG. 1. However, the images may be downloaded onto a computer, such as a laptop or PC, which has a processor, memory, user input and display, which operate for this purpose in the same way as those of the processing unit 106, and the further analysis of the images may be carried out on that computer under the control of dedicated software. It will be understood that the images may be retrieved from a PACS (picture archiving and communication system). Alternatively, or in addition, images may be transmitted to an external server for processing. The images may be anonymised prior to transmission.

Figure 4A:
FIG. 4A shows an end systole image captured by the echocardiography system shown in FIG. 1.
Figure 4B:
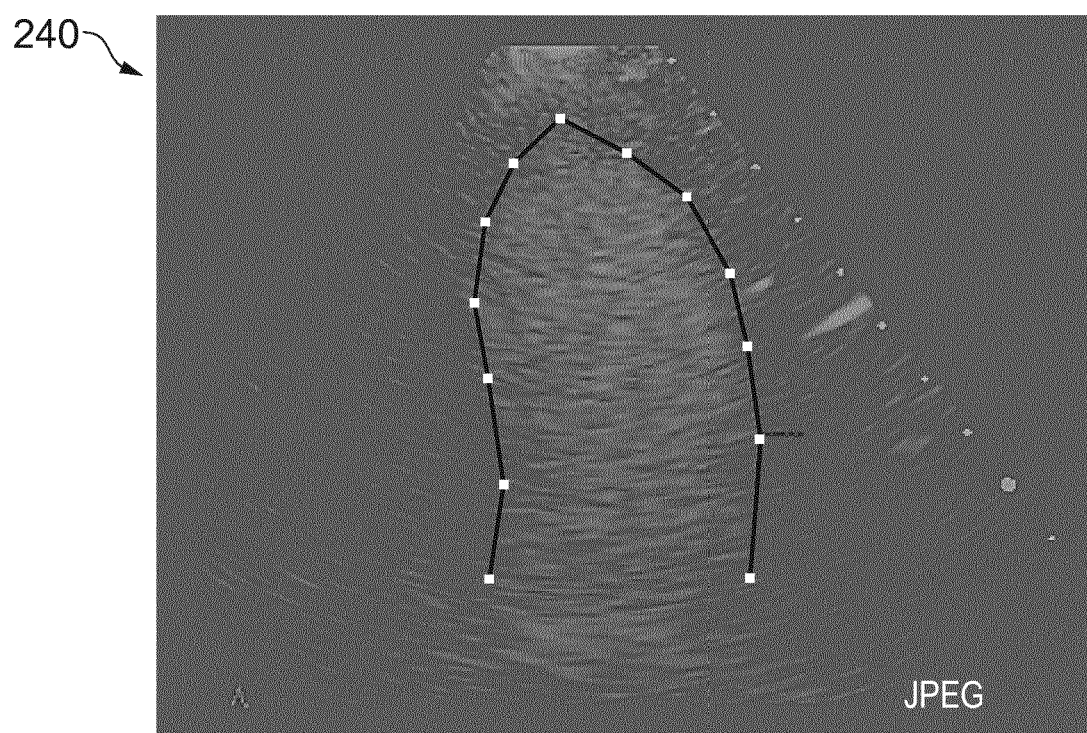
FIG. 4B shows an end diasystole image captured by the echocardiography system shown in FIG. 1.

The image closest to end systole, i.e. maximum contraction during the cardiac cycle, and the image closest to end diastole, i.e. maximum volume during the cardiac cycle, are identified for the left ventricle 202 (BLOCK 302). This can be done by a user viewing the images on the display 112 and selecting a first image 230 as closest to end systole (referred to herein as the end systole image 230), and a second image 240 as closest to end diastole (referred to herein as the end diastole image 240). The end systole image 230 and the end diastole image 240 are acquired at first and second times respectively in the cardiac cycle. An exemplary end systole image 230 is shown in FIG. 4A, and an exemplary end diastole image 240 is shown in FIG. 4B. The selection of the end systole image 230 and the end diastole image 240 may be made by the user on the basis of an assessment and comparison of the volume of the left ventricle 202 in each of the images as judged by eye, or by noting the points of opening and closing of the mitral valve, or using the QRS complex on an ECG plot, or by any combination of these. Alternatively, the processor 108 may be arranged to use image processing techniques to identify the end systole image 230 and the end diastole image 240. The image processing techniques may, for example, determine the volume of the left ventricle 202 in each of the images. The processor may identify the image with the smallest left ventricle volume as the end systole image 230; and the image with the largest left ventricle volume as the end diastole image 240. Alternatively, the image processing techniques may identify and track movements of image elements which are persistent across multiple images to identify the end systole image 230 and the end diastole image 240. The reversal in the direction of movement of the persistent image elements may be used to identify end systole and end diastole, for example. The end systole image 230 and the end diastole image 240 are identified in the memory 110, for example being marked with an appropriate flag, so that they can be selected and viewed by a user.

The inner wall 218 of the left ventricle 202 is identified at end systole in the end systole image 230, and at end diastole in the end diastole image 240 (BLOCK 304). The left ventricle 202 is contoured (or mapped) at end diastole in the end systole image 230 and at end systole in the end diastole image 240 (BLOCK 306). The contouring of the left ventricle 202 comprises identifying a plurality of end systole contour points 232-$n$ around the inner wall 218 in the end systole image 230; and a plurality of end diastole contour points 242-$n$ around the inner wall 218 in the end diastole image 240. A first continuous curve is plotted between the end systole contour points 232-$n$ to form an end systole contour line 233; and a second continuous curve is plotted between the end systole contour points 242-$n$ to form an end diastole contour line 243. The end systole contour line 233 and the end diastole contour line 243 may comprise straight lines and/or curved lines. The end systole contour line 233 and the end diastole contour line 243 may, for example, be profiled to match a boundary identified in the end systole image 230 and the end diastole image 240 respectively.

The end systole contour points 232-$n$ and the end systole contour line 233 form an end systole contour data set 234; and the end diastole contour points 242-$n$ and the end diastole contour line 243 form an end diastole contour data set 244. Each end systole contour point 232-$n$ in the end systole contour data set 234 is paired with a corresponding one of the end diastole contour points 242-$n$ in the end diastole contour data set 244. The resulting pairs of end systole and end diastole contour points 232-$n$, 242-$n$ represent changes in the motion of the wall of the heart 200 during a cardiac cycle. The pairs of end systole and end diastole contour points 232-$n$, 242-$n$ may correspond to the same feature of the left ventricle 202, albeit in different locations in the end systole image 230 and the end diastole image 240 due to the wall motion during the cardiac cycle. In the present embodiment, thirteen (13) end systole and end diastole contour points are identified in the end systole image 230 and the end diastole image 240. The end diastolic contour points and the end systolic contour points are labelled 1 to 13 according to their position along the endocardium (i.e. n=1, 2, 3, . . . 13). The end systole and end diastole contour data sets 234, 244 are combined, as shown in FIG. 5A.

Figure 5B:
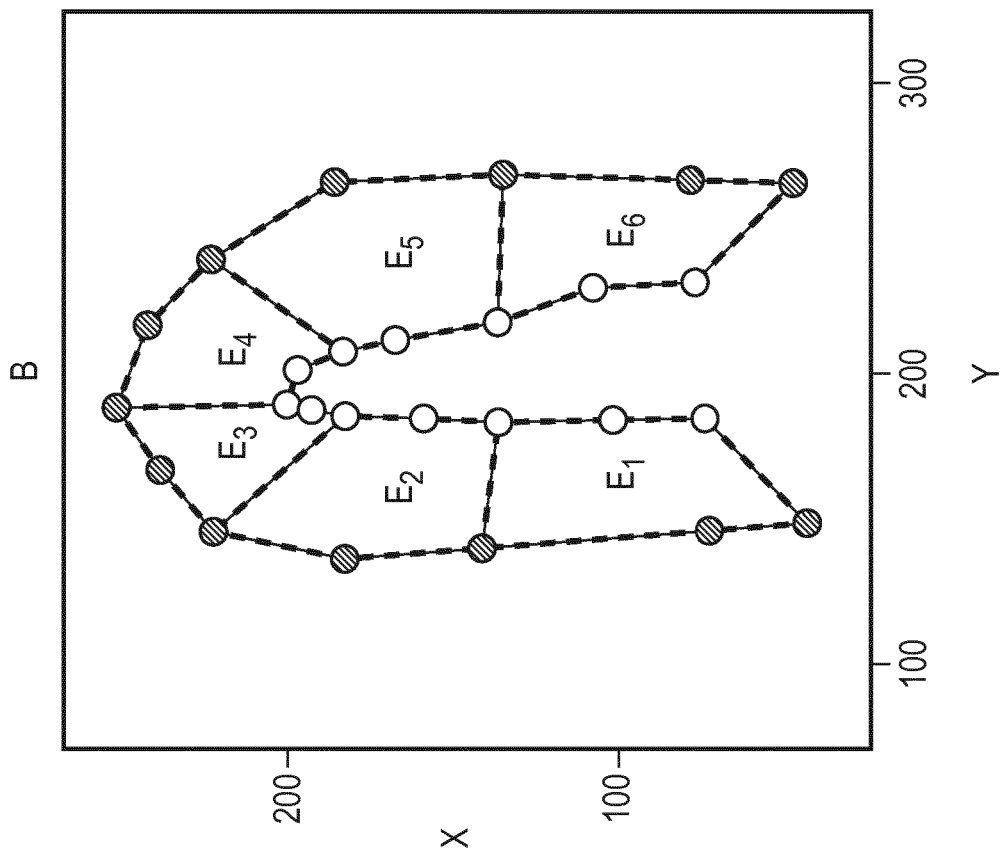
FIG. 5B shows a plurality of elements generated from the contour data sets shown in FIG. 5A.
Figure 5A:
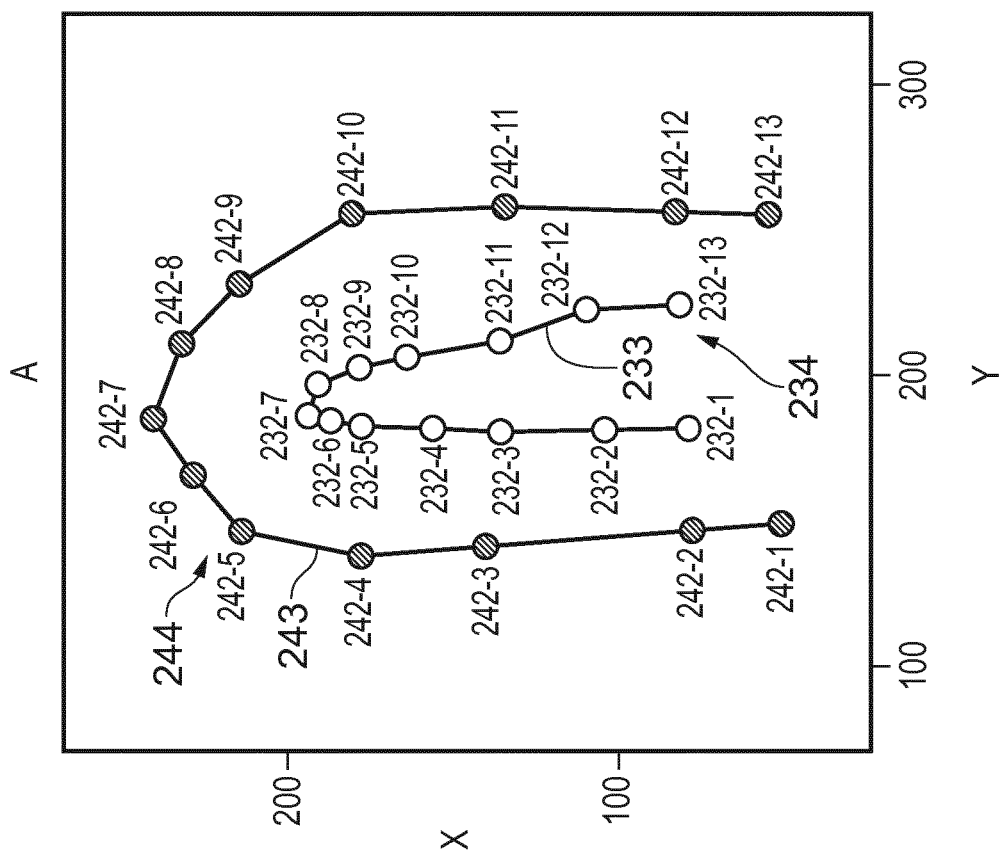
FIG. 5A shows contour data sets composed of end systole contour points and end diastole contour points.

As shown in FIG. 5B, the end systole contour points 232-$n$ and the end diastole contour points 242-$n$ form a plurality of elements $E_i$ (where i is a whole number) representing the cardiac cyclic motion of the internal wall (BLOCK 308). As described herein, the elements $E_i$ are analysed and scored to grade the cardiac cyclic motion of the corresponding section of the inner wall 218 of the left ventricle 202. In the illustrated arrangement, three (3) pairs of end systole contour points 232-$n$ and end diastole contour points 242-$n$ (i.e. three (3) end systole contour points 232-$n$ and three (3) end diastole contour points 242-$n$ from the respective end systole and end diastole contour data sets 234, 244) define each element $E_i$. In the illustrated example, the end systole image 230 and the end diastole image 240 are two-chamber apical images. The changes in the cardiac cyclic motion of the internal wall are represented by six (6) elements $E_{1-6}$. Each of the elements $E_{1-6}$ is in the form of a planar (two-dimensional) polygon. The elements $E_{1-6}$ correspond to a respective segment of the model of the left ventricle. In particular, a first element $E_1$ corresponds to the basal inferior segment; a second element $E_2$ corresponds to the mid inferior segment; a third element $E_3$ corresponds to the apical inferior segment; a fourth element $E_4$ corresponds to the apical anterior segment; a fifth element $E_5$ corresponds to the mid anterior segment; and a sixth element $E_6$ corresponds to the basal anterior segment. It will be understood that the cardiac cyclic changes may be represented by a different number of elements $E_i$, for example less than six (6) elements or more than six (6) elements.

The elements $E_i$ are analysed to generate at least one wall motion metric for scoring (i.e. classifying or grading) the cardiac cyclic motion of the corresponding sections of the heart 200 (BLOCK 310). The analysis of the elements $E_i$ is described in more detail herein. The generated metric is compared to a predefined reference data model to score the wall motion (BLOCK 312). The results of the scoring are then output, for example to a screen or display (BLOCK 314). The scoring may be reviewed by a clinician.

The contouring of the left ventricle 202 will now be described in more detail. The contouring may be performed by an echocardiographer; or using suitable image processing techniques. Echo images of a left ventricle 202 acquired with a contrast agent are shown in FIGS. 4A and 4B. The end systole image 230 is shown in FIG. 4A; and the end diastole image 240 is shown in FIG. 4B. The apex 212 of the left ventricle 202 can be located as the top of the left ventricle 202, and the base 216 of each side 222, 224 can be located from the shape of the inner wall 218. The longitudinal (Y) axis is defined as the reference line passing through the apex 212 and the midpoint between the base of the two sides 222, 224. The x axis can then be defined as the line perpendicular to the y axis half way between the apex and the midpoint between the two sides of the base 216. The mid-point on each side 222, 224 can be identified as the point where the x axis intersects the side wall on that side 222, 224. The intermediate end systole contour points 232-$n$ and the end diastole contour points 242-$n$ may be identified by subdividing the regions between the apex 212 and the mid-point on each side 222, 224; and by subdividing the region between the mid-point and the base on each side 222, 224.

As mentioned above, each of these end systole contour points 232-$n$ and the end diastole contour points 242-$n$ may be identified by a user. Alternatively, image processing may be used to identify the end systole contour points 232-$n$ and the end diastole contour points 242-$n$. If image processing is used, the outline of the left ventricle 202 is first identified as the boundary between the lighter area within the left ventricle 202 and the darker area of the myocardium forming the walls around it (or vice versa for images acquired without use of a contrast agent). Suitable algorithms for identifying such boundaries are well known. Once the boundary has been identified, the algorithm may then be arranged to identify the highest point (maximum y value) of the boundary as being the apex 212, and the points where the boundary changes direction at the lower end as the base 216. Again, algorithms for analysing the radius and direction of curvature, and how that changes around the boundary, can be used to identify these points, and the points at the lower end of the apex 212. The coordinates of each of the end systole contour points 232-$n$ and the end diastole contour points 242-$n$ are determined with reference to the coordinate system. The scale of the images acquired by the echocardiography system 100 is known. Thus, the coordinates of each of the end systole contour points 232-$n$ and the end diastole contour points 242-$n$ define the position of the point in the plane of the corresponding image. The distance between the contour points in each pair indicates the distance moved by the corresponding section of the heart 200 between end systole and end diastole.

The analysis of the elements $E_i$ to generate wall motion metrics will now be described with referenced to FIGS. 6A to 6D. As shown in FIG. 6A, each element $E_i$ is in the form of a polygon having n sides. As shown in FIG. 6A, an element area A of each element $E_i$ is calculated from the first and second sets of contour data 234, 244 by means of a shoelace formula:

$$A = \frac{1}{2}\left|\sum_{i=1}^{n-1} x_i y_{i+1} + x_n y_1 - \sum_{i=1}^{n-1} x_{i+1} y_i + x_1 y_n\right| \quad \text{(Equation 1)}$$

where n=the number of sides of the polygon; and
($x_i$, $y_i$)=the vertices of the polygon (i=1, 2, . . . , 6).

The calculated area A of each element $E_i$ is then normalised as a fraction of the total area represented by the total area of the end-diastolic contour points.

Figure 6B:
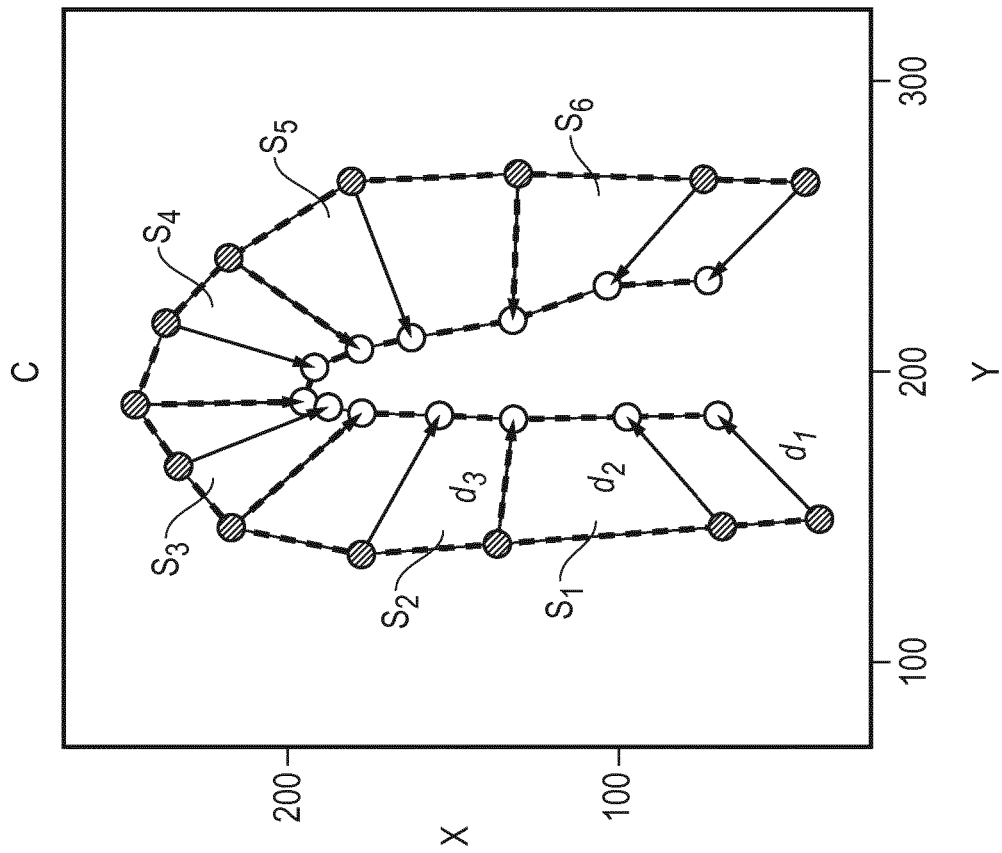
FIG. 6B illustrates generation of a mean distance metric for each element illustrated in FIG. 5B.
Figure 6A:
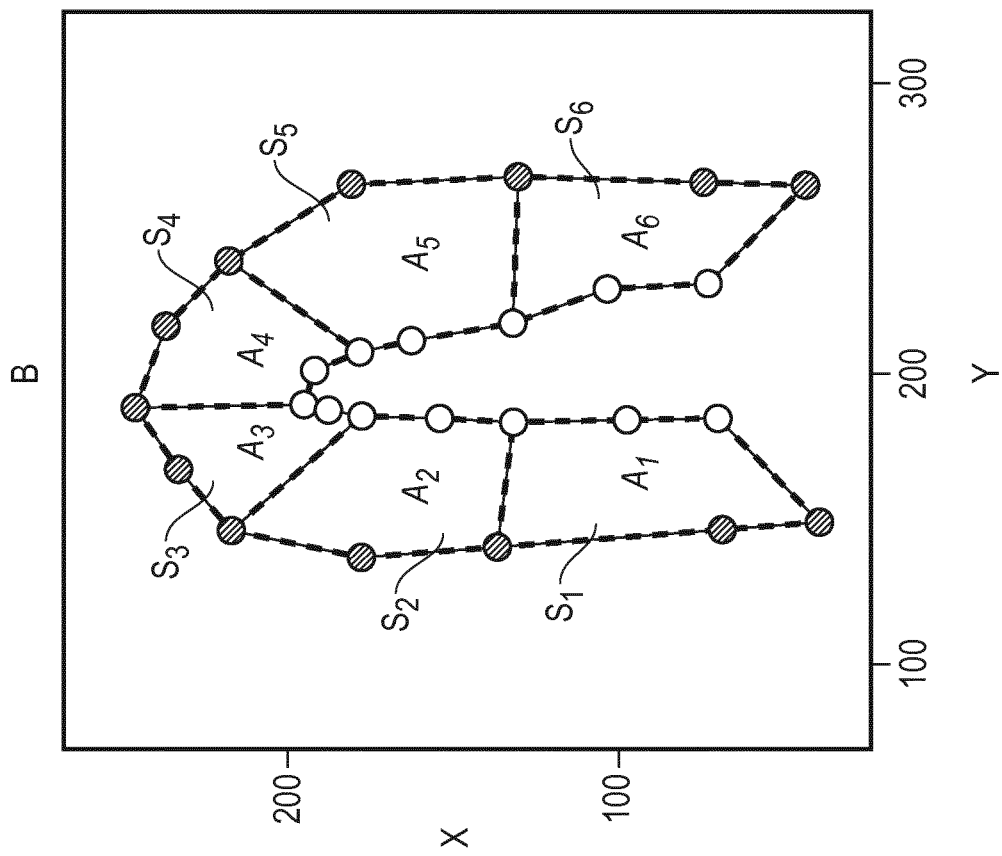
FIG. 6A illustrates generation of an area metric for each element illustrated in FIG. 5B.

As shown in FIG. 6B, the Euclidean distance (d) between each pair of end-diastolic and end-systolic end systole contour points 232-$n$ and the end diastole contour points 242-$n$ is computed using the equation:

$$d = \sqrt{\sum_{i=1}^{n}(q_i - p_i)^2} \quad \text{(Equation 2)}$$

where n=the number of dimensions;
p=the co-ordinates of the end diastolic contour point; and
q=the co-ordinates of the end systolic contour point.

The mean distance (d) for each element $E_i$ is then calculated (i.e., $\bar{x}(d_1, d_2, d_3)$ for the first element E1, $\bar{x}(d_3, d_4, d_5)$ for the second element E2, and so on). The mean distance is subsequently normalised as a fraction of the total perimeter distance of the end diastolic contour points.

Figure 6D:
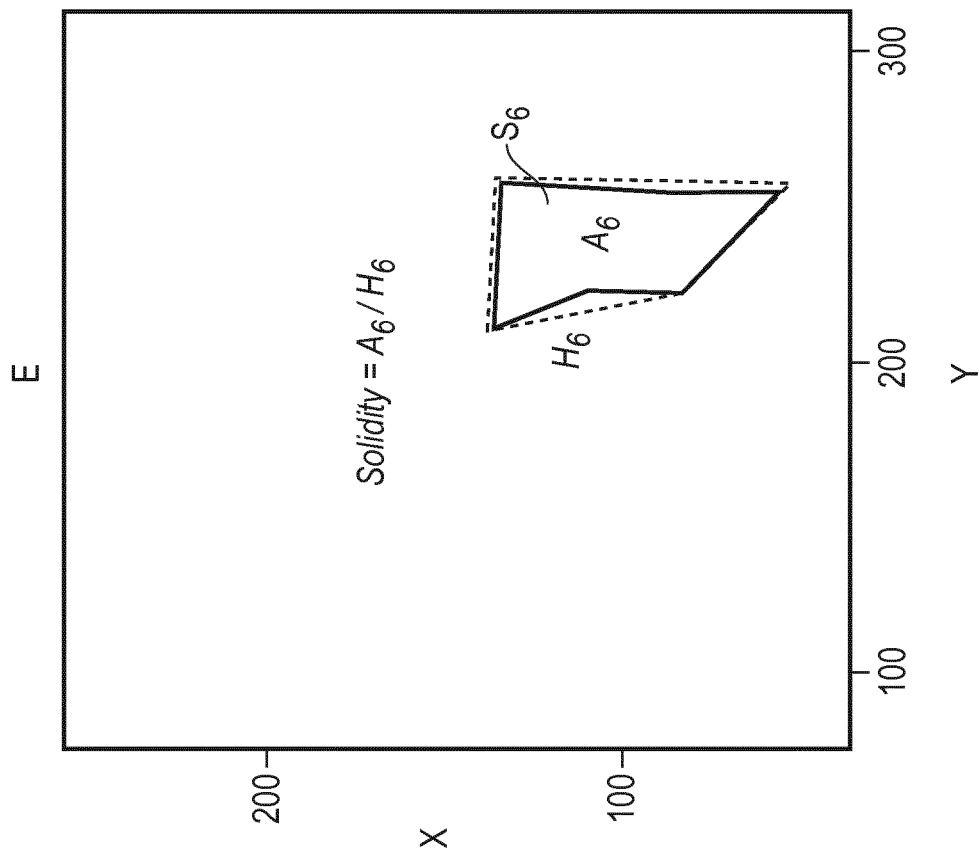
FIG. 6D illustrates generation of a solidity metric for each element illustrated in FIG. 5B.
Figure 6C:
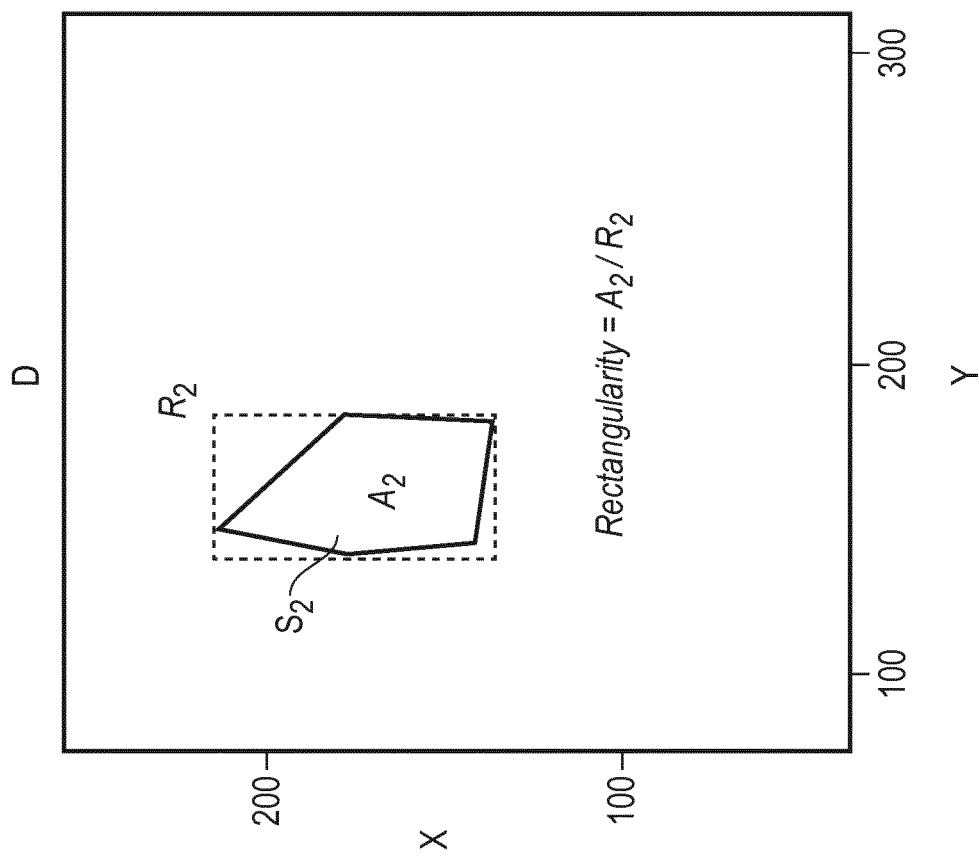
FIG. 6C illustrates generation of a rectangularity metric for each element illustrated in FIG. 5B.

As shown in FIG. 6C, a rectangularity of each element $E_i$ was calculated as the ratio between the area of each element ($A_i$) and the area of its minimum bounding rectangle ($R_i$):

$$\text{Rectangularity}_i = \frac{A_i}{R_i} \quad \text{(Equation 3)}$$

where $A_i$=area of each element $E_i$; and
$R_i$=area of the minimum bounding rectangle.

As shown in FIG. 6D, a solidity $S_i$ of each element $E_i$ was calculated as the ratio between the element's area ($A_i$) and the area of its convex hull ($H_i$):

$$S_i = \frac{A_i}{H_i} \quad \text{(Equation 4)}$$

where $A_i$=area of each element $E_i$; and
$H_i$=area of the corresponding convex hull.

In order to assess the correlation between the calculated metrics and the reference wall motion scores, a reference data set comprising raw (i.e. unprocessed) two-dimensional echocardiography data was analysed. The reference data set was composed of historic data comprising end diastolic images and end systolic images for a group of patients. The end diastolic images and the end systolic images were analysed in accordance with the techniques described herein to identify the end systole contour points 232-$n$ and the end diastole contour points 242-$n$. Elements $E_i$ corresponding to respective segments of a standard model of the left ventricle 202 were thereby identified. The elements $E_i$ were analysed using the techniques described herein to calculate the following metrics: normalised area A, normalised mean distance d, rectangularity, and solidity $S_i$. The metrics were generated for rest and stress conditions for each element $E_i$. The elements $E_i$ were also independently scored by two cardiologists using a standard scoring system consisting of the reference wall motion scores: normal ("1"), hypokinetic ("2"), akinetic ("3"), dyskinetic ("4"), and unable to score ("X"). Any scores that were discrepant between the two reference data sets were reviewed and a consensus reached. Elements with a wall motion score of "X" were removed from the reference data set (n=2). Due to the low number of elements in the available reference data set having a wall motion score of "4" (n=2), these were also removed from the analysis. Thus, in the present embodiment, each element $E_i$ from the reference data set was scored as normal ("1"), hypokinetic ("2"), akinetic ("3"). The analysis was repeated for s rest condition and a stress condition for each patient. As described herein, the metrics calculated through analysis of the raw reference data set are used to generate a reference data model against which the calculated metrics may be compared. The reference data model is generated for each element $E_i$. The reference data model may be a univariate model or a multivariate model. The reference data model may be stored in the memory 110 of the echocardiography system 100. Alternatively, the reference data set may be stored in the memory 110 and the reference data model generated by the processing unit 106. This approach may enable dynamic comparisons, for example in respect of particular metrics or combinations of metrics.

Figure 7A:
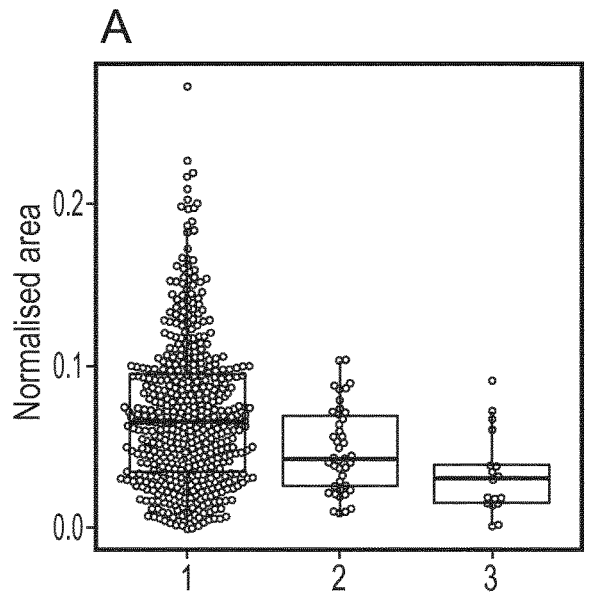
FIG. 7A illustrates the analysis of the area metric for a rest condition.
Figure 7B:
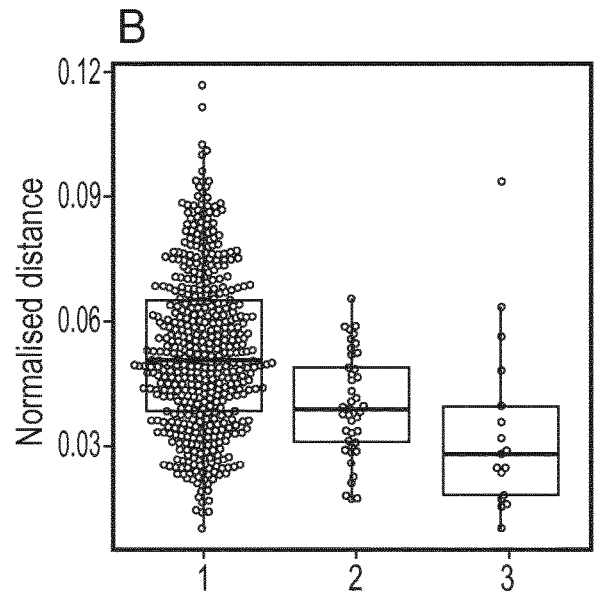
FIG. 7B illustrates the analysis of the mean distance metric for a rest condition.
Figure 7C:
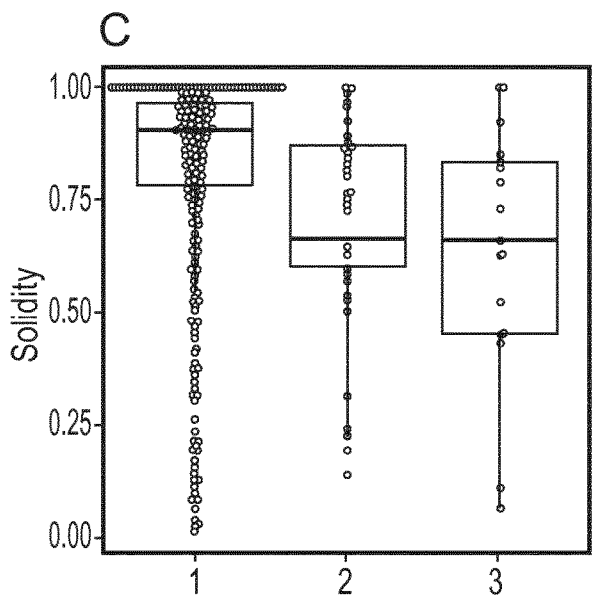
FIG. 7C illustrates the analysis of the rectangularity metric for a rest condition.
Figure 7D:
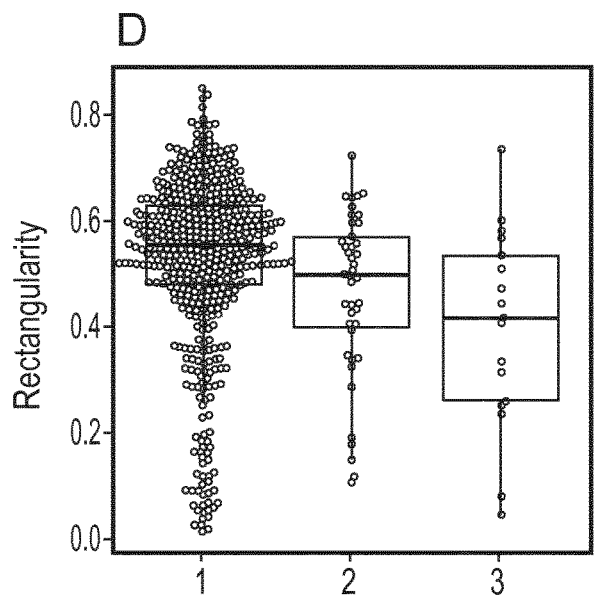
FIG. 7D illustrates the analysis of the solidity metric for a rest condition.

A plot of the calculated metrics for each element $E_i$ and the wall motion score allocated by the cardiologists (i.e. normal "1", hypokinetic "2", akinetic "3") for the rest condition are shown in FIGS. 7A-7D. The second quartile of the metrics is represented for each reference wall motion score by a box plot comprising a median line for that set of metrics. The normalised element area A for each reference wall motion score is shown in FIG. 7A. The normalised mean distances d for each reference wall motion score is shown in FIG. 7B. The calculated solidity for each reference wall motion score is shown in FIG. 7C. The calculated rectangularity for each reference wall motion score is shown in FIG. 7D. A Wilks-Lambda non-parametric, multivariate test statistic of $P<0.05$ is determined in each wall motion score group. A statistically significant correlation is identified between the calculated metrics and the allocated wall motion score.

Figure 8A:
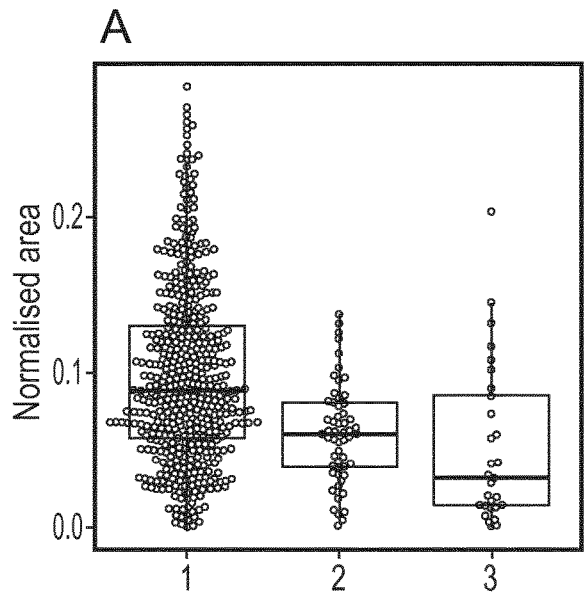
FIG. 8A illustrates the analysis of the area metric for a stress condition.
Figure 8B:
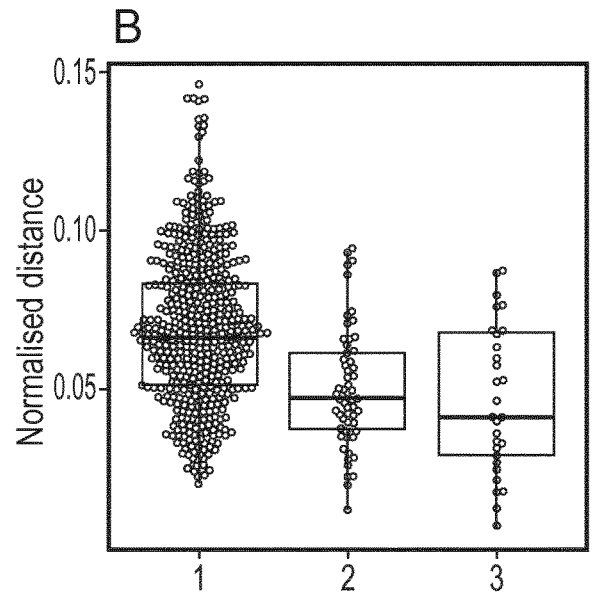
FIG. 8B illustrates the analysis of the distance metric for a stress condition.
Figure 8C:
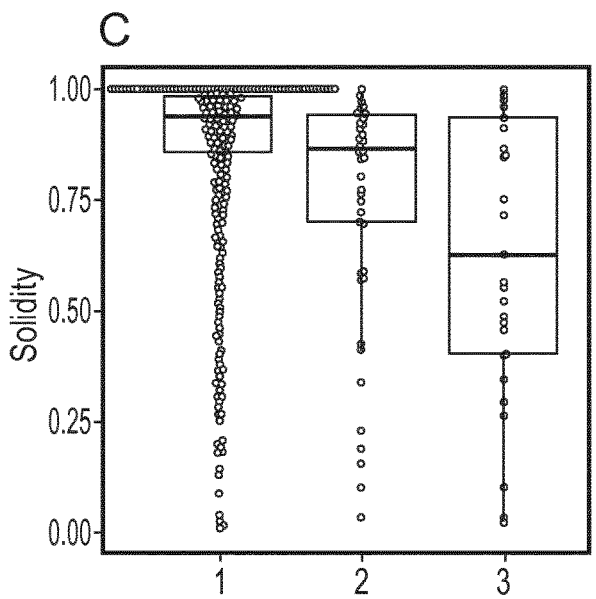
FIG. 8C illustrates the analysis of the rectangularity metric for a stress condition.
Figure 8D:
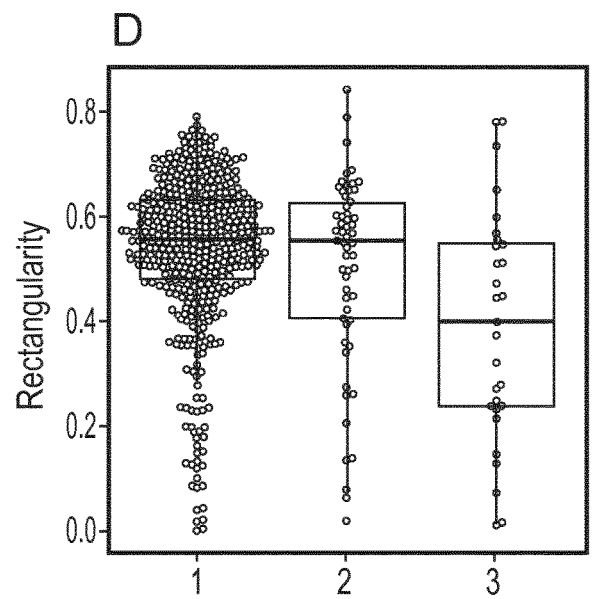
FIG. 8D illustrates the analysis of the solidity metric for a stress condition.

A plot of the calculated metrics for each element $E_i$ and the wall motion score allocated by the cardiologists (i.e. normal "1", hypokinetic "2", akinetic "3") for the stress condition are shown in FIGS. 8A-8D. The second quartile of the metrics is represented for each reference wall motion score by a box plot comprising a median line for that set of metrics. The normalised element area A for each reference wall motion score is shown in FIG. 8A. The normalised mean distances d for each reference wall motion score is shown in FIG. 8B. The calculated solidity for each reference wall motion score is shown in FIG. 8C. The calculated rectangularity for each reference wall motion score is shown in FIG. 8D. A Wilks-Lambda non-parametric, multivariate test statistic of $P<0.05$ is determined in each wall motion score group. A statistically significant correlation is identified between the calculated metrics and the allocated wall motion score.

The scoring for each element $E_i$ can be calculated in dependence on one of the calculated metrics. The processing unit 106 may be configured to define a univariate distribution, for example a univariate normal distribution. By way of example, the scoring can correspond to a z-score (standard score) for one of the calculated metrics. The z-score indicates how many standard deviations a calculated metric is from the population mean in units of standard deviation. The processing unit 106 may be configured to allocate a score to each element $E_i$ corresponding to the determined z-score. However, the accuracy of the score calculated for each element $E_i$ may be improved referencing two or more of the calculated metrics. The processing unit 106 may be configured to define a multivariate distribution, for example a multivariate normal distribution. The processing unit 106 may be configured to define a bivariate distribution or a higher dimensional distribution. The processing unit 106 may be configured to calculate a 'distance' of the calculated metric from a reference population. This technique enables analysis to be performed in higher dimensions. One approach is to use the distance from the first principal component of the data PC1. Alternatively, or in addition, the Mahalanobis distance may be calculated by the processing unit 106. Other statistical analysis techniques are also appropriate.

Figure 9A:
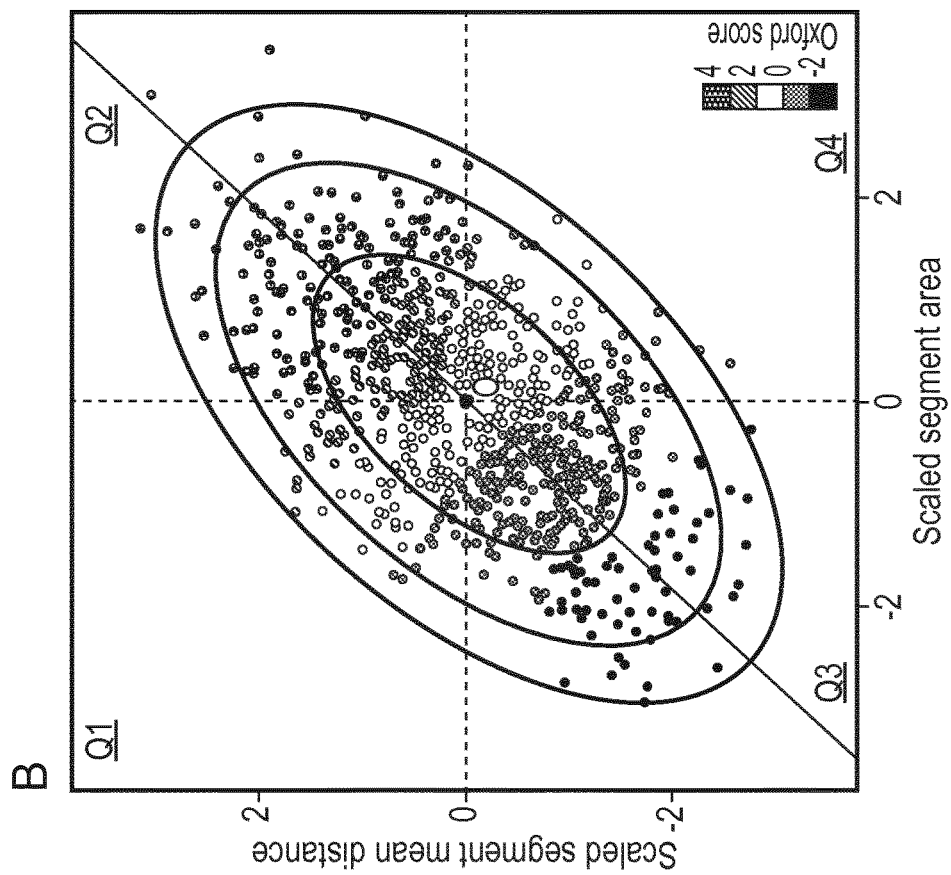
FIG. 9A illustrates a reference data model based on bivariate analysis of the normalised area and mean distance metrics.
Figure 9B:
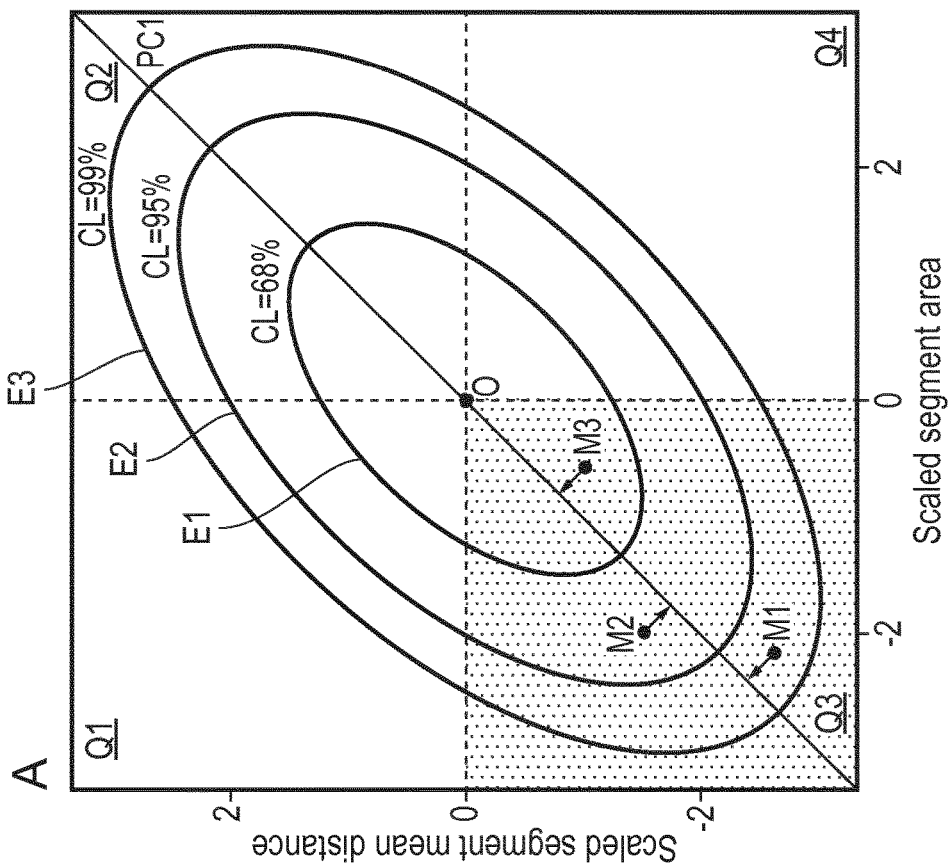
FIG. 9B shows a normally distributed data set applied to the reference data model illustrated in FIG. 9A.

By determining the correlation between the mean distance and the area of each element $E_i$, a score can be determined for the wall section corresponding to each element $E_i$. In the present embodiment, the scoring comprises a continuous scale, rather than the traditional scoring system which relies on discrete values. A mock representation of the correlation between z-scaled element areas and mean distances is illustrated in FIG. 9A. A lower left quadrant Q3 represents those elements $E_i$ identified as having potentially abnormal wall motion. A set of three (3) ellipses E1 to E3 represent the confidence intervals (CI) for the distribution of the data points: the inner ellipse E1 represents CI=68%, the middle ellipse E2 represents CI-95% and the outer ellipse $E_3$ represents CI=99%. A centroid O of the data is shown; and a line PC1 represents an orthogonal regression line through the data (i.e., the first principal component of the data PC1). A set of markers M1-M3 are representative of data points which are being scored. A set of randomly generated, normally distributed data with a covariance of 0.56 (n=1, 000) is illustrated in FIG. 9B. Each data point is coloured according to the continuous scoring determined in accordance with the analysis techniques described herein.

The processing unit 106 in accordance with the present embodiment implements a continuum approach for scoring each element $E_i$. The principal component models are constructed in dependence on the z-scaled metrics of each element $E_i$, as described herein. This is performed for each elements $E_i$ derived from the end systole image 230 and the end diastole image 240. The description herein focuses on the six (6) elements $E_i$ corresponding to the segments visible in the standard model of the two-chamber apical images. It will be understood that the same techniques may be implemented in respect of additional elements $E_i$ corresponding to other segments of the left ventricle 202, for example by analysis of three-chamber apical images and/or four-chamber apical images. The analysis is performed independently in respect of end systole and end diastole images 230, 240 acquired for rest and stress conditions. The processing unit 106 may compare the results of the analysis in respect of the rest and stress conditions.

The scoring of the elements $E_i$ in dependence on a bivariate analysis based on two calculated metrics is visualised in FIGS. 9A and 9B. The metrics in the present case are the normalised area and the mean distance of each element $E_i$. A reference data model is generated in dependence on the normalised area and the mean distance of the elements $E_i$ identified through analysis of the reference data set. In the present case, only those elements with an allocated wall motion score of "1" were included in the generation of the reference data model. In order to generate a score for a given element $E_i$, the processing unit 106 calculates the corresponding metrics for that element $E_i$. The processing unit 106 calculates the normalised area and the mean distance of elements $E_i$ identified through analysis of the end systole image 230 and the end diastole image 240 for a patient. The implementation described herein with reference to FIGS. 9A and 9B utilises bivariate analysis based on the normalised area and the mean distance of each element $E_i$. It will be understood that other combinations of the metrics may be used for scoring each element $E_i$. For example, the bivariate analysis may combine the mean distance and solidity metrics; or the normalised area and rectangularity metrics.

Figure 10A:
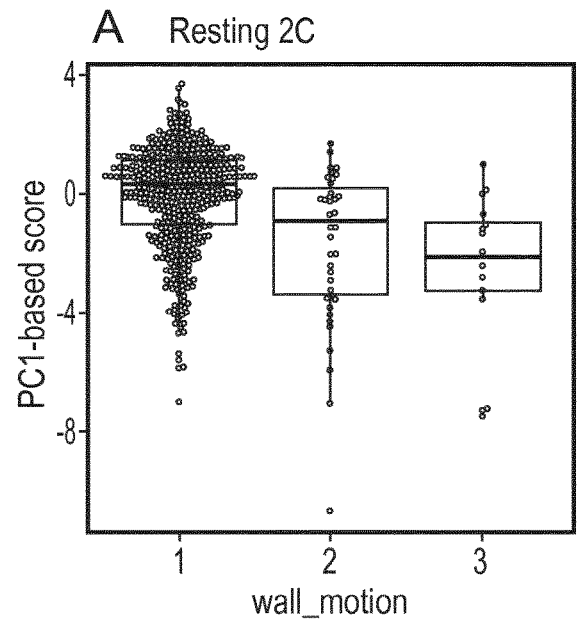
FIG. 10A illustrates the multivariate analysis of each of the metrics for a first rest condition in a two-chamber apical image.
Figure 11A:
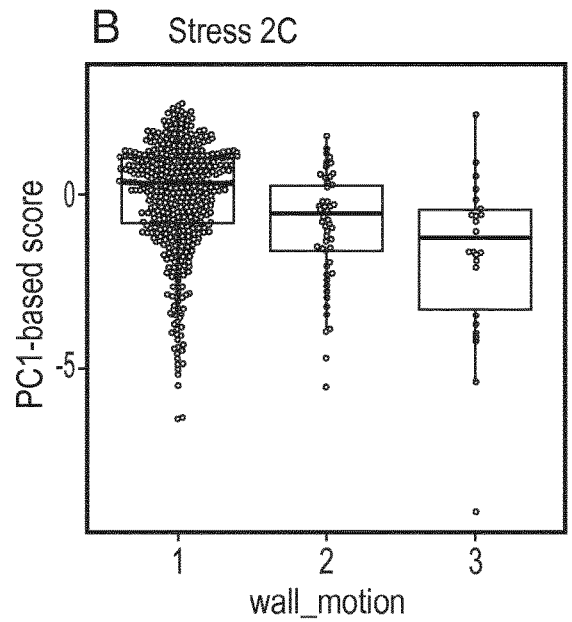
FIG. 11A illustrates the multivariate analysis of each of the metrics for a first stress condition in a two-chamber apical image.
Figure 10B:
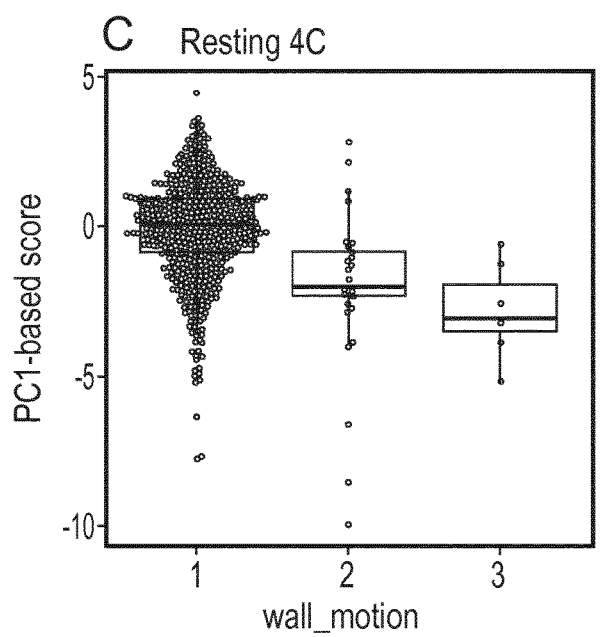
FIG. 10B illustrates the multivariate analysis of each of the metrics for a second rest condition in a four-chamber apical image.
Figure 11B:
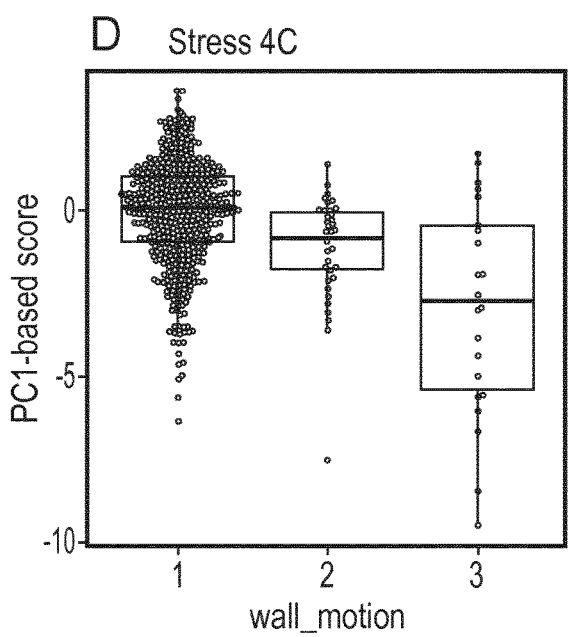
FIG. 11B illustrates the multivariate analysis of each of the metrics for a second stress condition in a four-chamber apical image.

The processing unit 106 may be configured to perform multivariate analysis. The processing unit 106 may be configured to combine each of the metrics described herein, namely: the normalised area A, the normalised mean distance d, the rectangularity, and the solidity $S_i$. The score for each element $E_i$ may be calculated in dependence on the multivariate analysis of the four (4) calculated metrics. Plots of the score calculated in dependence on a first principal component PC1 and the allocated wall motion score (i.e. normal "1", hypokinetic "2", akinetic "3") are shown in FIGS. 10, 10B, 11A and 11B. A plot of the score calculated in dependence on a first principal component PC1 of the multivariate analysis of a rest condition in a two-chamber apical image is illustrated in FIG. 10A. A plot of the score calculated in dependence on a first principal component PC1 of the multivariate analysis of a rest condition in a four-chamber apical image is illustrated in FIG. 10B. A plot of the score calculated in dependence on a first principal component PC1 of the multivariate analysis of a stress condition in a two-chamber apical image is illustrated in FIG. 11A. A plot of the score calculated in dependence on a first principal component PC1 of the multivariate analysis of a stress condition in a four-chamber apical image is illustrated in FIG. 11B.

Figure 12A:
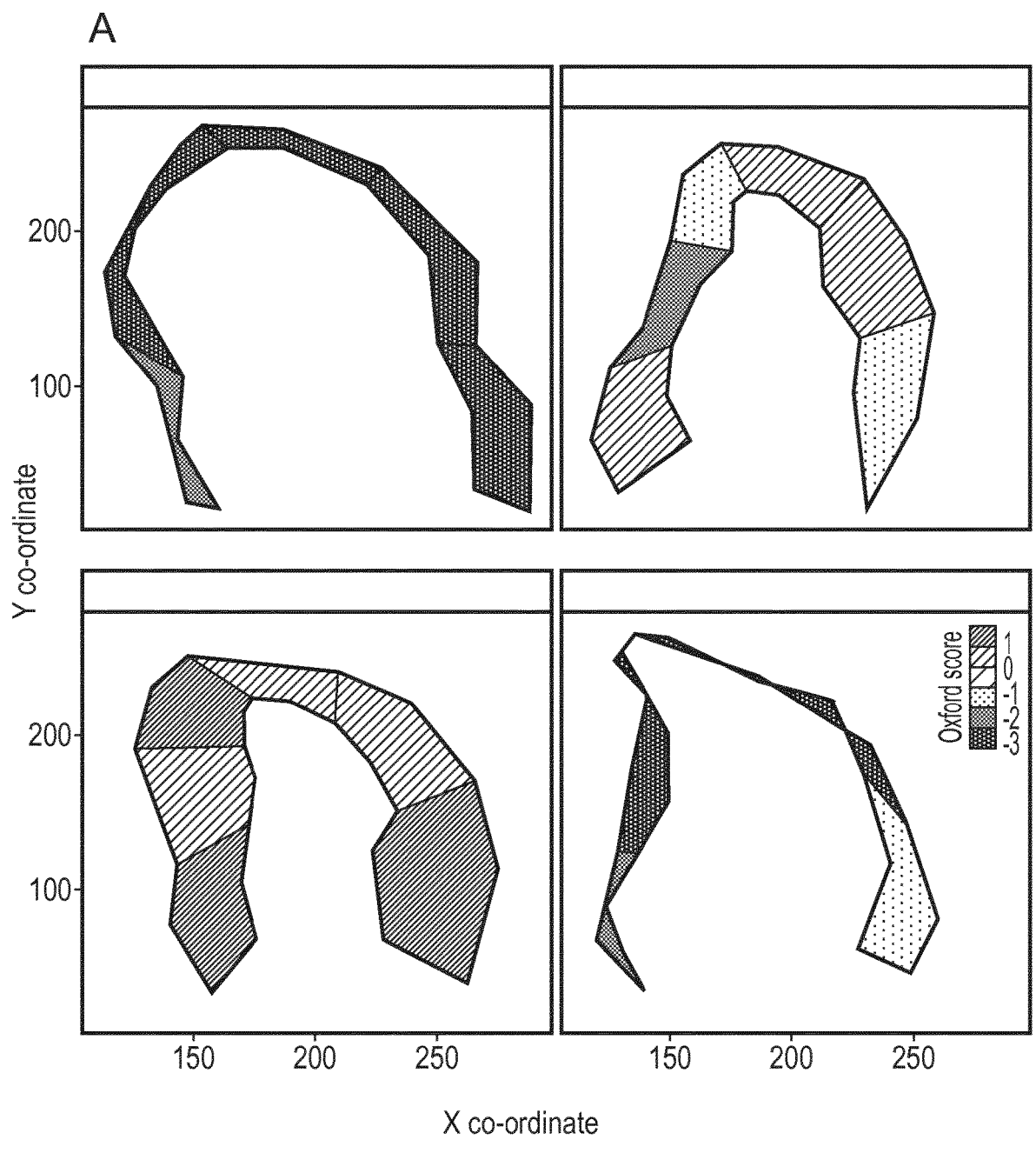
FIG. 12A shows scoring applied to elements in a rest condition.
Figure 12B:
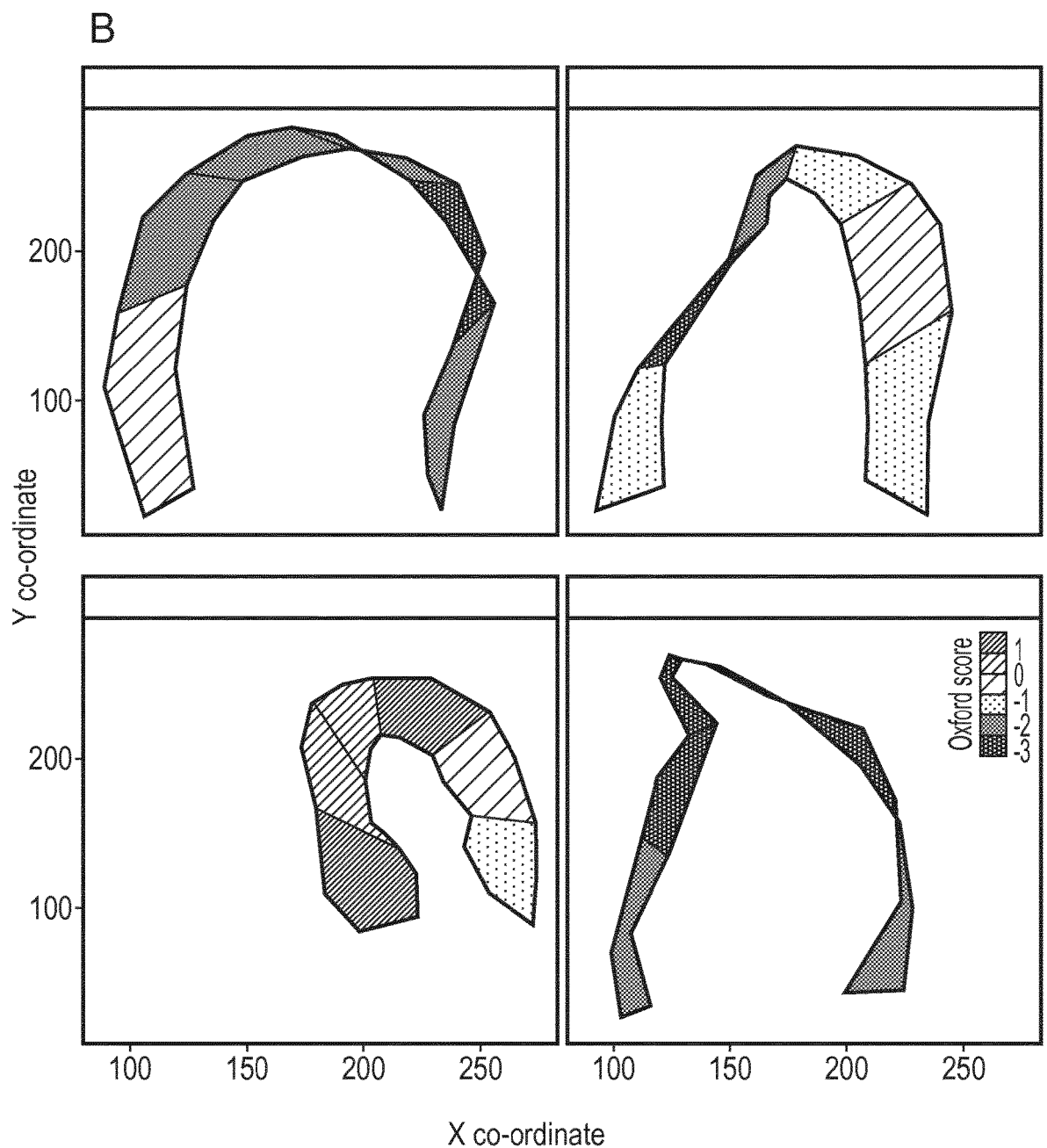
FIG. 12B shows scoring applied to elements in a stress condition.

The calculated metrics for each element $E_i$ are compared to the reference data model for a corresponding element $E_i$. The score for each element $E_i$ is calculated in dependence on this comparison. The score represents a value of the first principal component of the new data; i.e. how far the calculated metrics are from the centroid of the data and thus how different they are from the reference data. The score can be calculated on a continuous scale. An example of this can be seen in FIGS. 12A and 12B where each element has been shaded according to the continuous scoring scale described herein. The scored images shown in FIG. 12A represent two chamber data for a rest condition; and the scored images shown in FIG. 12B represent two chamber data for a stress condition.

The processing unit 106 may be configured to calculate different metrics for scoring each element $E_i$. These metrics may be used in addition to, or instead of the metrics described herein for the univariate and multivariate analysis. The processing unit 106 may, for example, calculate one or more of the following metrics: shear; strain; coefficient of variation of the distances in an element; and aspect ratio. The processing unit 106 may also calculate a distance metric other than the distance between the pairs of points described herein. For example, the processing unit 106 may calculate the distance between diametrically opposed points within the same element; or the distance between corresponding points in different elements (i.e. between Ei and Ei+j).

The processing unit 106 has been described with particular emphasis on the analysis of the element $E_i$ in one image to calculate the metrics. It will be understood that the processing unit 106 may analyse multiple images. The different images may contain the same element $E_i$. The processing unit 106 may be configured to compare the scores generated for a particular element $E_i$ in dependence on the analysis of the different images. If a discrepancy is detected between the scores, this can be flagged up as a potential problem with image quality or similar. This may enable the quality of the different images to be checked. Similarly, particularly with fine-grained elements $E_i$, the scores calculated for elements $E_i$ disposed proximal to each other are typically related. If an expected relationship is identified, this can be flagged as a potential image quality issue. These techniques may enable identification of an image of one or more of the element $E_i$, which is more likely to be correct.

The processing unit 106 may analyse the elements $E_i$ visible in one or more images to infer the behaviour of elements $E_i$ which are not visible. For example, a score may be estimated for an unsighted element $E_i$ in dependence on a calculated score for at least one element $E_i$ disposed adjacent to or proximal to the unsighted element $E_i$. Further analysis may be performed to build up a complete model of the left ventricle 202 based on the available views. The resulting model may enable scoring to be inferred from one or more nearby elements $E_i$.

The statistical analysis described herein was performed within the R statistical computing environment (v3.4.1), making use of the ggplot2, dplyr, ggbeeswarm, Momocs, pathmapping, and ggpubr packages. Due to the imbalance in the number of observations between groups in each comparison, multivariate, non-parametric hypothesis tests were employed to compare group means using the npmv package. A type I error rate ($\alpha$) of 0.05 was used for all comparisons.

The processing unit 106 has been described herein as calculating metrics for elements $E_i$ corresponding to the segments of a standard model of the left ventricle 102. It will be understood that the techniques described herein do not require that the elements $E_i$ correspond to the segments. For example, the elements $E_i$ may be smaller than the segments of the standard model. The elements $E_i$ may correspond to sub-segments of the standard model. By reducing the size of the elements $E_i$, the scoring may provide a more precise indication of the location of abnormalities in the cardiac cyclic motion. For example, it is envisaged that the scoring may indicate the location of an abnormal function within one of the segments of the standard model, for example highlighting a position near a boundary of the segment or in a central location.

As described herein, a reference data model is generated by analysing a reference data set comprising raw two-dimensional echocardiography data. In the embodiment described above, the reference data set comprises historic data comprising end diastolic images and end systolic images for a group of patients. In a further development, the reference data set used to generate the reference data mode may be updated iteratively. For example, the analysis of new echocardiographs may be incorporated into the reference data set to increase the available data population. Thus, the reference data model may continue to be refined as additional data becomes available. The iterative development of the reference data model may allow for pathological changes and patient evolution.

The analysis described herein is performed independently for each element $E_i$. However, it will be appreciated that the analysis may be modified to consider the relationship between a plurality of elements $E_i$. For example, the analysis may simultaneously score the motion of first and second elements $E_i$ which are disposed adjacent to each other or in opposition to each other, for example on opposing sides of the left ventricle 202.

The reference data model described herein may also be modified in dependence on outcome data available in respect of some or all of the reference data set. The term "outcome data" is used herein to refer to diagnostic information. The outcome data is associated with a corresponding record or set of data in the reference data set. The diagnostic information may, for example, relate to angiographic data and/or cardiac events for a patient. The outcome data may indicate whether the patient had a positive or negative diagnosis for a cardiac condition, for example the presence or absence of coronary artery disease, during an elapsed time interval. The outcome data may, for example, be generated one (1) year, two (2) years or three (3) years after acquisition of the echocardiography data.

A weighting of the data within the reference data set may be adjusted in dependence on the outcome data. For example, a weighting applied to the data within the reference data set for which outcome data is available may be increased or decreased to change the statistical significance thereof. The weighting may be adjusted in dependence on the period of time elapsed between acquisition of the echocardiograph image and a subsequent diagnostic event. In a variant, the reference data model could be generated exclusively in dependence on data for which outcome data is available. The reference data model could be generated exclusively in dependence on data for which the outcome data indicates the presence or absence of a particular condition, such as coronary artery disease. The outcome data may be used to filter the reference data set to generate different reference data models.

The processing unit 106 may be configured also to provide a diagnostic function to generate a diagnostic output. A diagnostic system is disclosed in the Applicant's International patent application PCT/GB2017/051720, the contents of which are incorporated herein in their entirety by reference. It has been recognised that the diagnostic function may utilise the outcome data described herein. The diagnostic function may also rely on one or more of the metrics generated for the wall motion score. By way of example, the rectangularity of each element $E_i$ may be used as a feature in the diagnostic model. The use of outcome data when generating a diagnostic model may help to take account of different disease proportions and characteristics over time and/or at different medical sites. For example, different sites may record different proportions of positive ('Disease') to negative ('Normal') outcomes. By utilising the outcome data in generating a diagnostic model, allowances may be made for these types of variations. The results of stress echo test (as determined by a cardiologist during/shortly after the test) may not always be accurate. An analysis undertaken by the Applicant of one (1) year outcome accuracy has shown an average inaccuracy of 7.2% in stress echo results across multiple data sets. By referencing outcome data over a period of time, the accuracy of the diagnostic model may be improved, thereby enabling mode accurate prediction of whether or not an individual will go on to develop a disease, such as coronary artery disease. The use of outcome data is believed to be patentable independently. This enhanced diagnostic functionality will now be described as a development of the previous embodiment. Like reference numerals are used for like components.

As described herein, each end systole contour point 232-n is paired with a corresponding one of the end diastole contour points 242-n in the end diastole contour data set 244. The resulting pairs of end systole and end diastole contour points 232-n, 242-n represent changes in the motion of the wall of the heart 200 during a cardiac cycle. Once the end systole and end diastole contour points 232-n, 242-n have been identified, their x and y coordinates in the Cartesian coordinate system may be stored in the memory 110, for example as an end systole coordinate set including the coordinates of the points on the end systole image and an end diastole coordinate set including the coordinates of the points on the end diastole image. The processor may be configured to calculate, from the two coordinate sets, the transformation in geometry of the left ventricle 202 between end systole and end diastole.

The processing unit 106 is configured to calculate values for various parameters that quantify the movement of the left ventricle 202 between end systole and end diastole. The calculation may include working out how far each point has moved in each of the x and y directions, by working out the change in position (End diastole−End systole) along both the x axis and the y axis. This gives a set of x axis movements $\Delta x$ and a set of y axis movements $\Delta y$ for each corresponding pair of end systole and end diastole contour points 232-n, 242-n. Each of these values may be a simple distance with no indication of direction. The mean change of all the points in both the x axis ($\Delta X$) and y axis ($\Delta Y$) may then be calculated separately so as to provide an average $\Delta x$ value or x direction movement $\Delta X$, and an average $\Delta y$ value or y direction movement $\Delta Y$ for the entire left ventricle 202. If each of the individual movement values are purely distance, without any indication of whether they are in the positive or negative x or y direction, then these averages will describe the total amount of movement, but not give an indication of the direction or of whether different parts of the LV wall are moving in the same direction or opposite directions.

Another parameter that may be calculated for each pair of end systole and end diastole contour points 232-n 242-n is the mean of the x and y direction movements $\Delta x$ and $\Delta y$, where the mean value for each point $\Delta xy = (\Delta x + \Delta y)/2$. The mean of all the values of $\Delta xy$ for all points can then be calculated to a value for the entire ventricle $\Delta XY$. This calculation is similar to the calculation of shear strain and is therefore referred to herein as the shear transformation. It will be appreciated that, for a given distance of movement, this parameter will be largest for movements at 45 degrees to both of the x and y axes, and smallest for movements along one of the axes.

A further parameter that can be calculated is similar to the principal transformation that can be calculated from x and y strain components, and is therefore referred to herein as the principal transformation, given by $$\text{Principal transformation} = C1(\Delta X + \Delta Y - \sqrt{(\Delta X + \Delta Y)^2 + C2\Delta XY^2})$$

where C1 and C2 are constants. The constant C1 may, for example, be ½ and the constant C2 may be 4. These values are used in the examples described below.

This transformation is closely related to the shear transformation and therefore tends to vary in a similar way to that parameter, but has a negative value indicating contraction of the heart. However, as indicated by the test results below, the principal transformation value can give a more reliable diagnosis in some cases, in particular of coronary artery disease (CAD).

It will be appreciated that each of these parameters relates to changes between end systole and end diastole in a single coronary cycle. However in stress echocardiography, (or corresponding tests carried out with other imaging methods)

there will be one value for each parameter for the heart at rest and one value for the heart at stress. Comparing those values, for example determining the difference between them, gives further information about heart function that can be used in diagnosis.

Once the x and y movements, and shear and principal transformation values have been calculated, the processor is then configured to compare these with reference values stored in the memory 110 to make a diagnosis of one or more specific heart conditions, and to generate a diagnostic output. The output may be a simple binary output indicating a positive or negative diagnosis. The processor unit 106 may be arranged to display the output on the display 112. Alternatively, or in addition, it may be arranged to store the output as data in association with the images on which it was based, for example by adding output data, indicative of the diagnosis, to a file in which the images are stored.

The reference values may be determined by means of a learning algorithm which, for example, can be run on the processor unit 106, and which uses a database of stress echo images with associated diagnoses as determined by conventional methods, which may be stored in the memory 110. Specifically, the database may include a large number of sets of images, each set comprising an end systole image and an end diastole image for both rest condition and stress condition, together with, for each set of images, an associated diagnosis, such as a positive or negative diagnosis for coronary artery disease (CAD). The learning algorithm may be arranged to analyse the images to calculate values of the various parameters described above, and then to determine the correlation between the diagnosis and the values of each of the various parameters.

Analysis was carried out on sample images from seventy (70) subjects. All results generated were from an apical four chamber view. Firstly the values were compared for positive and negative outcomes as determined from the DSE results. Then the comparison was repeated with the DSE results corrected for confirmed false positives in the DSE results.

Table 1 Shows values of the principal transformation (in mm), shear transformation value (in mm), and mean ΔX (in mm) at rest and stress for DSE outcome (1=Pos, 2=Neg) in the Apical four Chamber view.

| Group Statistics | | | | | |
|---|---|---|---|---|---|
| | DSE_Result | N | Mean | Std. Deviation | Std. Error Mean |
| Stress_Prin | 1.00 | 9 | −6.8214 | 4.08788 | 1.36263 |
| | 2.00 | 61 | −8.9260 | 2.20018 | .28170 |
| Rest_Prin | 1.00 | 9 | −7.7332 | 3.86497 | 1.28832 |
| | 2.00 | 61 | −9.3163 | 2.41589 | .30932 |
| Rest_Shr | 1.00 | 9 | 17.7267 | 9.16943 | 3.05648 |
| | 2.00 | 61 | 21.5356 | 5.50610 | .70498 |
| Stress_Shr | 1.00 | 9 | 17.0074 | 8.06969 | 2.68990 |
| | 2.00 | 61 | 22.2608 | 4.56871 | .58496 |
| Rest_X | 1.00 | 9 | 18.8694 | 11.02116 | 3.67372 |
| | 2.00 | 61 | 21.8492 | 6.65078 | .85155 |
| Stress_X | 1.00 | 9 | 19.9334 | 9.80639 | 3.26880 |
| | 2.00 | 61 | 25.8710 | 7.43965 | .95255 |

Table 2 Shows means of Principal transformation value (in mm), Shear transformation (in mm) and X transformation (in mm) at rest and stress for Adjusted DSE outcome (1=Pos, 2=Neg).

| Group Statistics | | | | | |
|---|---|---|---|---|---|
| | Adjusted_DSE | N | Mean | Std. Deviation | Std. Error Mean |
| Stress_Prin | 1.00 | 7 | −4.4716 | 1.29120 | .48803 |
| | 2.00 | 63 | −9.1203 | 2.24588 | .28295 |
| Rest_Prin | 1.00 | 7 | −5.3352 | 1.21275 | .45838 |
| | 2.00 | 63 | −9.5325 | 2.44136 | .30758 |
| Rest_Shr | 1.00 | 7 | 12.0645 | 2.74525 | 1.03761 |
| | 2.00 | 63 | 22.0438 | 5.58342 | .70344 |
| Stress_Shr | 1.00 | 7 | 12.2348 | 3.81629 | 1.44242 |
| | 2.00 | 63 | 22.6243 | 4.44025 | .55942 |
| Rest_X | 1.00 | 7 | 11.6937 | 2.73459 | 1.03358 |
| | 2.00 | 63 | 22.5519 | 6.84823 | .86280 |
| Stress_X | 1.00 | 7 | 14.1727 | 4.81157 | 1.81860 |
| | 2.00 | 63 | 26.3226 | 7.29318 | .91885 |

Table 3 shows independent samples T-Test for variables vs adjusted DSE.

| Independent Samples Test | | | | | | |
|---|---|---|---|---|---|---|
| | | Levene's Test for Equality of Variances | | | | |
| | | F | Sig. | t | df | Sig. (2-tailed) |
| Stress_Prin | Equal variances assumed | 1.705 | .196 | 5.356 | 68 | .000 |
| | Equal variances not assumed | | | 8.240 | 10.596 | .000 |
| Rest_Prin | Equal variances assumed | 2.355 | .130 | 4.466 | 68 | .000 |
| | Equal variances not assumed | | | 7.604 | 12.377 | .000 |
| Rest_Shr | Equal variances assumed | 2.106 | .151 | −4.644 | 68 | .000 |
| | Equal variances not assumed | | | −7.961 | 12.527 | .000 |
| Stress_Shr | Equal variances assumed | .194 | .661 | −5.942 | 68 | .000 |
| | Equal variances not assumed | | | −6.715 | 7.923 | .000 |
| Rest_X | Equal variances assumed | 5.696 | .020 | −4.136 | 68 | .000 |
| | Equal variances not assumed | | | −8.065 | 16.500 | .000 |
| Stress_X | Equal variances assumed | .927 | .339 | −4.290 | 68 | .000 |
| | Equal variances not assumed | | | −5.963 | 9.395 | .000 |

From the values of the various parameters obtained from the sample data, machine learning may be used to determine the accuracy of each parameter as an indicator of adjusted Dobutamine stress echo (DSE) outcome. Using the data above, a J48 pruned decision tree with 10 fold cross validation method was used to classify the data. The accuracy of each parameter as an indicator of diagnostic outcome is summarized in the tables below, in which the following abbreviations are used: TP=true positive; FP=false positive; FN=false negative; TN=true negative; PPV=positive predictive value; and NPV=negative predictive value.

TABLE 4

Accuracy of Consultant Interpretation

| J48 | TP = 6 | FN = 1 |
|---|---|---|
| Accuracy = 94.3% | FP = 3 | TN = 60 |
| Sensitivity = 85.7% | | PPV = 66.7% |
| Specificity = 95% | | NPV = 98.4% |

TABLE 5

Accuracy of Stress Principal Transformation for Adjusted DSE outcome

| J48 Value = −5.95 | TP = 7 | FN = 0 |
|---|---|---|
| Accuracy = 95.7% | FP = 3 | TN = 60 |
| Sensitivity = 100% | | PPV = 70% |
| Specificity = 95.2% | | NPV = 100% |

TABLE 6

Accuracy of Rest Principal Transformation for Adjusted DSE outcome

| J48 Value = −6.92 | TP = 5 | FN = 2 |
|---|---|---|
| Accuracy = 88.6% | FP = 6 | TN = 57 |
| Sensitivity = 71.4 | | PPV = 45.5% |
| Specificity = 90.5% | | NPV = 96.6% |

TABLE 7

Accuracy of Stress Shear Transformation for Adjusted DSE outcome

| J48 Value = 15.85 | TP = 6 | FN = 1 |
|---|---|---|
| Accuracy = 95.7% | FP = 2 | TN = 61 |
| Sensitivity = 85.7% | | PPV = 85.7 |
| Specificity = 96.8% | | NPV = 98.4 |

TABLE 8

Accuracy of Rest Shear Transformation for Adjusted DSE Outcome

| J48 Value = 15.35 | TP = 5 | FN = 2 |
|---|---|---|
| Accuracy = 91.4% | FP = 4 | TN = 59 |
| Sensitivity = 71.4 | | PPV = 55.6% |
| Specificity = 93.7% | | NPV = 96.7% |

Figure 13:
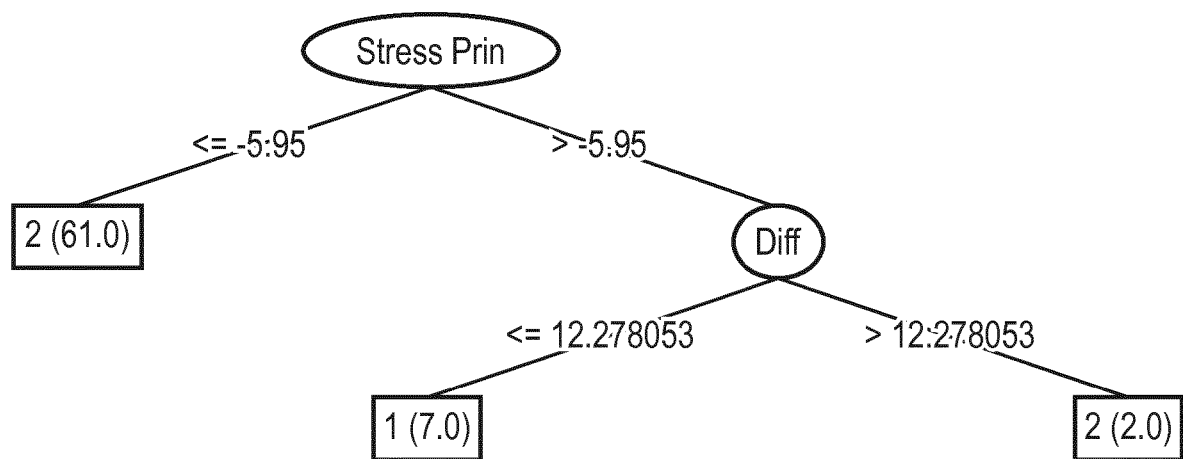
FIG. 13 shows a decision tree composed of a series of decision points defining threshold values.

Then from all of the variables, using machine learning, a decision tree which is shown in FIG. 13 was derived to provide accurate diagnosis from the data. The decision tree defines a series of decision points, each of which defines a reference or threshold value of a parameter. The decision tree outlines a simple algorithm which operates as follows. Firstly the principal transformation of the left ventricle 202 as described above is determined for the stress condition of the heart. If the transformation is less than −5.95 mm (i.e. a negative value with magnitude greater than 5.95 mm) then the diagnosis is negative. If the value is greater than −5.95 mm (i.e. a negative value with magnitude greater than 5.95 mm) then difference in principal transformation between rest and stress conditions is greater than 12.278053 mm then the diagnosis is negative, but if it is less than that distance, the diagnosis is positive. It will be appreciated that the structure of the decision tree, and the reference or threshold values at each decision point in the decision tree, will depend on the diagnosis that is to be made.

The processing unit 106 described above implements a fixed (static) diagnostic model for diagnosing coronary artery disease. As illustrated in FIG. 13, the decision tree defines a series of decision points, each of which defines a reference or threshold value of a parameter. The processing unit 106 may implement a dynamic diagnostic model. The reference or threshold values at each decision point in the decision tree may be modified dynamically, for example to reflect the new echocardiographic data and/or outcome data. At least in certain embodiments, this may provide improved diagnostic functions.

The new echocardiographic data may be incrementally added to the existing set of reference data. The new data is used to expand the data population and may progressively change the diagnostic model. The reference or threshold values used in the decision tree may be updated to reflect the available echocardiographic data. The iterative development of the reference data allows the diagnostic model to change with respect to time. It will be understood that the decision tree described herein may be replaced with other analysis tools, such as a supervised machine learning model.

The outcome data comprises diagnostic information for each patient, for example relating to angiographic data and/or cardiac events. The outcome data in the present embodiment indicates whether the presence or absence of coronary artery disease was detected during an elapsed time interval after acquisition of the end systole image and end diastole image used in the reference data set. The outcome data may, for example, be generated one (1) year, two (2) years, three (3) years or longer after acquisition of the echocardiography data. The outcome data in the present embodiment is generated one (1) year after acquisition of the echocardiography data. The outcome data is compiled by considering any angiographic data and cardiac events that have taken place during the elapsed time interval. It will be understood that the outcome data continues to evolve with respect to time. The outcome data may, therefore, be updated on an ongoing basis, for example on an annual basis or when a classification changes. By updating the outcome data, the diagnostic tools and diagnostic models generated in dependence on the reference data may be adjusted dynamically to represent pathological changes and patient evolution.

In order to implement the dynamic diagnostic model, a classification model is built using a supervised machine learning algorithm. The outcome data is used to label the reference data accessed by the machine learning algorithm. The machine learning algorithm uses the labels to distinguish between different classifications. In the present embodiment, the classifications correspond to the presence or absence of coronary artery disease.

Alternatively, or in addition, the classifications may grade a particular condition, for example in dependence on an identified stenosis level or percentage. It will be understood that the classifications may distinguish between other conditions When generating the diagnostic models, the machine learning algorithm may adjust the relative weighting of the reference data in dependence on the labels derived from the outcome data. At least in certain embodiments, updating the reference data in dependence on the outcome data may provide improved diagnostic accuracy based on the stress echocardiograms.

In order to build a diagnostic model, a set of features are calculated from the contour data. The features are calculated per-segment (for example by analysing one or more of the elements $E_i$ described herein) and optionally in respect of the entire left ventricle 202. The available feature-set is analysed to identify those features that are most relevant. The most pertinent features may thereby be identified to build the diagnostic model. In the case of a random forest (which consists of multiple decision trees), the identified features form the decision nodes. The most relevant features may vary across geographic regions and/or change as the disease evolves, the features identified for use in the model may change. Even if the features remain the same, the thresholds and weightings may change. As shown in Tables 1 and 2 herein, the top feature remains unchanged as the ejection fraction at peak stress. However, the next most important features changes for the different conditions. In the first data set (Table 1), the volume change between end-systole and end-diastole is the next most relevant. However, in the combined dataset, the area of a specific segment at rest in the two-chamber view is the next most relevant. In order to train the model, the reference data needs to be labelled. In view of the potential inaccuracies, using the results of a stress echo (as determined by a cardiologist) as the label will not necessarily lead to an accurate model. The use of outcome data that is collected a period of time after the acquisition of the reference data (for example, one (1) year after acquisition of the echocardiograph images), at least some of these deficiencies can be overcome or ameliorated.

The outcome data can be collected for different periods of time. The outcome data can, at least in certain embodiments, provide an indication of how far in advance the effects of coronary artery disease can be identified. Moreover, multiple classes of labels can be used to predict different disease severity. As more outcome data is accumulated, the diagnostic model is updated to help ensure that the classification remains as accurate as possible due to the possibility of disease evolution and population changes. This can be done by retraining the entire model every time new outcome data is received. In practice, this may prove time-consuming. As an alternative, incremental machine learning techniques can be implemented by the processor to continually update the diagnostic model.

The implementation of the classification model will now be described with reference to a first reference data set and a second reference data set. The first data set comprises a first set of one hundred and twenty-four (124) stress echocardiograms (collected in Oxford between May 2011 and August 2013). The second data set comprises a set of three hundred and thirty-nine (339) stress echocardiograms from a separate study (collected between March 2015 and August 2016 in six (6) different hospitals across the Thames Valley). The outcome data is compiled one (1) year after acquisition of the stress echocardiograms. The outcome data generates a binary outcome value. In particular, an outcome is considered positive if during the elapsed one (1) year interval one of the following events is identified:
  (i) a cardiac event (e.g. myocardial infarction);
  (ii) an angiogram which showed greater than 70% stenosis.

The outcome is considered negative if neither of the aforementioned events (i) or (ii) occurred in the elapsed one (1) year interval. In the first data set, ten (10) positive outcomes were identified, and in the second data set thirteen (13) positive outcomes were identified.

The Boruta package from the R statistical computing environment to assess the most relevant features for predicting an outcome. The Boruta package performs feature selection by comparing the importance of attributes to those possible at random. A standard implementation comprising a random forest with 500 trees was implemented. Table 9 details the most important features and their mean importance score for the first dataset. The second data set was added to the first data set. Table 10 details the most important features and their mean importance score for the combined first and second data sets. The most relevant features change as more data is available for processing. This demonstrates that the classification model may change with the addition of more reference data. It is believed that these changes would be more pronounced if the additional reference data is acquired at a later date and/or over a more widespread geographical area. Although the use of a random forest model has been described herein, it will be understood that another model could be used, or indeed an ensemble of models.

TABLE 9

Most relevant features using the first data set

| Feature | Mean importance |
| --- | --- |
| EF_P<br>Ejection fraction at peak stress | 6.23 |
| ES_P_to_ED_P<br>Ratio of end-systolic to end-diastolic peak volume | 6.20 |
| rect_segment_4_R_2C<br>Rectangularity of the apical anterior segment at rest | 5.42 |
| solid_segment_4_R_2C<br>Solidity of the apical anterior segment at rest | 5.41 |
| norm_area_segment_4_R_2C<br>Normalised area of the apical anterior segment at rest | 5.35 |
| ES_P_to_ED_P_2C<br>Ratio of the end-systolic to end-diastolic 2 chamber area at peak stress | 5.00 |
| ES_P_to_ED_P_4C<br>Ratio of the end-systolic to end-diastolic 4 chamber area at peak stress | 4.70 |
| P_ES<br>End-systolic volume at peak stress | 4.53 |
| total_ES_area_P_2C<br>2 chamber end-systolic area at peak stress | 3.86 |
| dy_8_P_4C<br>Euclidean distance of the eighth point in 4 chamber at peak stress | 3.75 |

TABLE 10

Most relevant features using combined data from the first and second data sets

| Feature | Mean importance |
| --- | --- |
| EF_P<br>Ejection fraction at peak stress | 6.59 |
| norm_area_segment_4_R_2C<br>Normalised area of the apical anterior segment at rest | 6.53 |

TABLE 10-continued

Most relevant features using combined data from the first and second data sets

| Feature | Mean importance |
| --- | --- |
| ES_P_to_ED_P_4C<br>Ratio of the end-systolic to end-diastolic 4 chamber area at peak stress | 6.38 |
| norm_area_segment_4_P_4C<br>Normalised area of the apical anterior segment at rest | 5.05 |
| total_ES_area_P_4C<br>4 chamber end-systolic area at peak stress | 4.30 |
| ES_P_to_ED_P<br>Ratio of the end-systolic to end-diastolic area at peak stress | 4.10 |
| prin_trans_P_4C<br>Principal strain in the 4 chamber view at peak stress | 3.96 |
| solid_segment_4_R_2C<br>Solidity of the apical anterior segment at rest | 3.96 |
| norm_d_segment_6_P_4C<br>Normalised average distance in the basal lateral segment | 3.94 |
| ES_P_to_ED_R_4C<br>Ratio of the end-systolic to end-diastolic 4 chamber area at peak stress | 3.91 |

The implementation of a continued learning strategy capable of incorporating new reference data may provide a more robust and accurate diagnostic model may be achieved. By incorporating the new reference data incrementally, the need to retrain the entire model may be reduced or avoided each time new data becomes available (which can prove a time-consuming process, particularly as the size of the reference data set increases). Moreover, the diagnostic model can adapt to changing disease characteristics over time. This is particularly important as the most relevant biomarkers may change over time due to the changing environments and lifestyles of the population, and the model needs to adapt to account for these. The dynamic diagnostic model can adapt to changing facets and characteristics of cardiovascular disease, thereby providing a robust and accurate prediction model.

The dynamic diagnostic model described herein utilises outcome data acquired over a one (1) year period. It will be understood that the outcome data may be accumulated over different periods of time. By combining the outcome data over a longer time period, the predictive power of the dynamic diagnostic model over a longer time period may be assessed.

The present application has been described with reference to cardiovascular disease. However, it will be understood that the methods and apparatus described herein may have other applications. For example, diagnostic tools may be developed to adapt to the changing imaging biomarkers for a tumour if the environment changes and the tumour size, appearance or calcification changes. Furthermore, the techniques may be applicable in imaging systems other than echocardiographs.

It will be appreciated that various modifications may be made to the embodiment(s) described herein without departing from the scope of the appended claims.

The invention claimed is:

1. A system for scoring motion of a heart wall, the system comprising:
an imaging system operable to acquire a first image of the heart wall at a first time and a second image of the heart wall at a second time;
a processor configured to:
identify a first set of contour data in the first image;
identify a second set of contour data in the second image;
in dependence on the first and second sets of contour data, define at least one element representing a cardiac cyclic change in a section of the heart wall;
analyse each element to generate two or more metrics, wherein the analysis of each element comprises determining a rectangularity of each element, said rectangularity being calculated as the ratio between the area of each element and the area of its minimum bounding rectangle; and
compare the two or more metrics generated for each element with a reference data model to score the motion of the corresponding section of the heart wall, the reference data model comprising a first principal component;
wherein the scoring comprises calculating a score for each element in dependence on bivariate or multivariate analysis of the two or more metrics generated for that element, the score representing a value of the two or more metrics on the first principal component of the reference data model.

2. A system as claimed in claim 1, wherein the processor is configured to identify a plurality of pairs of contour points, each pair of contour points relating to a corresponding feature in the first and second sets of contour data.

3. A system as claimed in claim 2, wherein each element comprises at least first and second pairs of contour points, the contour points in each pair defining vertices of the element.

4. A system as claimed in claim 3, wherein the analysis of each element comprises determining a distance between the contour points in each pair and calculating a mean distance between the contour points for each element.

5. A system as claimed in claim 2, wherein each element comprises opposing first and second sides corresponding to motion trajectories of the contour points.

6. A system as claimed in claim 1, wherein the analysis of each element comprises determining an area of the element.

7. A system as claimed in claim 1, wherein the imaging system is configured to generate two-dimensional images; the first and second images comprising two-dimensional images of the heart wall.

8. A system as claimed in claim 1, wherein each element comprises a polygon.

9. A system as claimed in claim 1, wherein the processor is configured to score the motion of the heart wall during a rest condition and during a stress condition.

10. A system as claimed in claim 1, wherein the first image comprises an end systole image and the second image comprises an end diastole image; the first set of contour data comprising end systole contour data and the second set of contour data comprising end diastole data.

11. A system for scoring motion of a heart wall, the system comprising:
an imaging system operable to acquire a first image of the heart wall at a first time and a second image of the heart wall at a second time;
a processor configured to:
identify a first set of contour data in the first image;
identify a second set of contour data in the second image;
in dependence on the first and second sets of contour data, define at least one element representing a cardiac cyclic change in a section of the heart wall;

analyse each element to generate two or more metrics, wherein the analysis of each element comprises determining a solidity of each element, said solidity being calculated as the ratio between the element's area and the area of its convex hull; and compare the two or more metrics generated for each element with a reference data model to score the motion of the corresponding section of the heart wall, the reference data model comprising a first principal component;

wherein the scoring comprises calculating a score for each element in dependence on bivariate or multivariate analysis of the two or more metrics generated for that element, the score representing a value of the two or more metrics on the first principal component of the reference data model.

12. A system as claimed in claim 11, wherein the processor is configured to identify a plurality of pairs of contour points, each pair of contour points relating to a corresponding feature in the first and second sets of contour data.

13. A system as claimed in claim 12, wherein each element comprises at least first and second pairs of contour points, the contour points in each pair defining vertices of the element.

14. A system as claimed in claim 13, wherein the analysis of each element comprises determining a distance between the contour points in each pair and calculating a mean distance between the contour points for each element.

15. A system as claimed in claim 12, wherein each element comprises opposing first and second sides corresponding to motion trajectories of the contour points.

16. A system as claimed in claim 11, wherein the analysis of each element comprises determining an area of the element.

17. A system as claimed in claim 11, wherein the imaging system is configured to generate two-dimensional images; the first and second images comprising two-dimensional images of the heart wall.

18. A system as claimed in claim 11, wherein each element comprises a polygon.

19. A system as claimed in claim 11, wherein the processor is configured to score the motion of the heart wall during a rest condition and during a stress condition.

20. A system as claimed in claim 11, wherein the first image comprises an end systole image and the second image comprises an end diastole image; the first set of contour data comprising end systole contour data and the second set of contour data comprising end diastole data.

* * * * *